(12) United States Patent
Hielscher et al.

(10) Patent No.: US 11,992,301 B2
(45) Date of Patent: May 28, 2024

(54) MONITORING TREATMENT OF PERIPHERAL ARTERY DISEASE (PAD) USING DIFFUSE OPTICAL IMAGING

(71) Applicant: The Trustees of Columbia University in the City of New York, New York, NY (US)

(72) Inventors: Andreas H. Hielscher, Brooklyn, NY (US); Christopher J. Fong, New York, NY (US); Jennifer Hoi, Belmont, CA (US); Hyun K. Kim, Cresskill, NJ (US); Michael Khalil, Miami Lake, FL (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 17/881,844

(22) Filed: Aug. 5, 2022

(65) Prior Publication Data
US 2023/0031593 A1    Feb. 2, 2023

Related U.S. Application Data

(63) Continuation of application No. 16/093,775, filed as application No. PCT/US2017/029027 on Apr. 23, 2017, now Pat. No. 11,439,312.
(Continued)

(51) Int. Cl.
*A61B 5/00*    (2006.01)
*A61B 5/02*    (2006.01)
(Continued)

(52) U.S. Cl.
CPC .............. *A61B 5/0261* (2013.01); *A61B 5/00* (2013.01); *A61B 5/0073* (2013.01);
(Continued)

(58) Field of Classification Search
CPC combination set(s) only.
See application file for complete search history.

(56) References Cited

U.S. PATENT DOCUMENTS

| 7,248,909 B2 | 7/2007 | Lee et al. |
| 8,082,015 B2 | 12/2011 | Yodh et al. |
| (Continued) | | |

FOREIGN PATENT DOCUMENTS

| WO | 2012065140 A2 | 5/2012 |
| WO | 2016015009 A9 | 3/2016 |
| WO | 2016081262 A2 | 5/2016 |

OTHER PUBLICATIONS

Durduran et al., "Diffuse Optics for Tissue Monitoring and Tomography," Rep. Prog. Phys., vol. 73, No. 7, pp. 76701 Jul. 2010.
(Continued)

*Primary Examiner* — Joel F Brutus
(74) *Attorney, Agent, or Firm* — Potomac Law Group, PLLC

(57) ABSTRACT

A plurality of modules are simultaneously positioned at locations that correspond to different angiosomes. Each of these modules has a front surface shaped and dimensioned for contacting a person's skin, a plurality of different-wavelength light sources aimed in a forward direction, and a plurality of light detectors aimed to detect light arriving from in front of the front surface. Each module is supported by a support structure (e.g., a strap or a clip) that is shaped and dimensioned to hold the front surface adjacent to the person's skin at a respective position. Perfusion in each of the angiosomes is monitored using these modules, and the surgeon can rely on this information to guide his or her intervention.

14 Claims, 21 Drawing Sheets

Related U.S. Application Data

(60) Provisional application No. 62/417,741, filed on Nov. 4, 2016, provisional application No. 62/326,822, filed on Apr. 24, 2016.

(51) Int. Cl.

| | | |
|---|---|---|
| *A61B 5/021* | (2006.01) | |
| *A61B 5/022* | (2006.01) | |
| *A61B 5/0225* | (2006.01) | |
| *A61B 5/0245* | (2006.01) | |
| *A61B 5/026* | (2006.01) | |
| *A61B 5/1455* | (2006.01) | |

(52) U.S. Cl.
CPC .............. *A61B 5/0075* (2013.01); *A61B 5/02* (2013.01); *A61B 5/02007* (2013.01); *A61B 5/021* (2013.01); *A61B 5/022* (2013.01); *A61B 5/02255* (2013.01); *A61B 5/0245* (2013.01); *A61B 5/1455* (2013.01); *A61B 5/6828* (2013.01); *A61B 5/6829* (2013.01); *A61B 5/6831* (2013.01); *A61B 5/6884* (2013.01); *A61B 5/7425* (2013.01); *A61B 2560/0437* (2013.01); *A61B 2562/04* (2013.01)

(56) References Cited

U.S. PATENT DOCUMENTS

| | | | |
|---|---|---|---|
| 9,351,686 | B1 | 5/2016 | Lash et al. |
| 9,398,870 | B2 | 7/2016 | Bechtel et al. |
| 2006/0063995 | A1 | 3/2006 | Yodh et al. |
| 2009/0118622 | A1 | 5/2009 | Durkin et al. |
| 2011/0190586 | A1 | 8/2011 | Kemp |
| 2013/0190596 | A1 | 7/2013 | Oraevsky et al. |
| 2013/0289394 | A1* | 10/2013 | Hielscher ............ A61B 5/0053 600/425 |
| 2014/0243691 | A1 | 8/2014 | Osaki et al. |
| 2016/0029900 | A1* | 2/2016 | LaPlante ............ A61B 5/02233 600/490 |
| 2016/0100781 | A1 | 4/2016 | Bechtel et al. |

OTHER PUBLICATIONS

Hirsch et al, "Peripheral arterial disease detection, awareness, and treatment in primary care," JAMA 286(11), 1317-1324 (2001).

International Search Report and Written Opinion issued in application No. PCT/US2017/029027 dated Jul. 3, 2017.

Johansson et al., "Scanning, non-contact, hybrid broadband diffuse optical spectroscopy and diffuse correlation spectroscopy system," Biomedical Optics Express, vol. 7, No. 2, pp. 481-498, Feb. 2016.

Khalil et al., "Detection of Peripheral Arterial Disease Within the Foot Using Vascular Optical Tomographic Imaging: A Clinical Pilot Study," Eur. J. Vasc. Endovasc. Surg, vol. 49, pp. 83-89, Jan. 2015.

Khalil et al., "Dynamic diffuse optical tomography imaging of peripheral artery disease," Biomedical Optics Express, vol. 3, No. 9, p. 2288, Sep. 2012.

Lee et al., "Broadband diffuse optical spectroscopy assessment of hemorrahage- and hemoglobin-based blood substitute resuscitation," Journal of Biomedical Optics, vol. 14, No. 4, p. 044027, Jul./Aug. 2009.

Mesquita et al., "Direct Measurement of tissue blood flow and metabolism with diffuse optics," Phil. Trans.R. Soc. A, vol. 369, pp. 4390-4406, Nov. 2011.

Mohler, "Screening for peripheral artery disease," Circulation, vol. 126, pp. 111-112, Aug. 2012.

Nagashima et al., "Development of a new instrument to measure oxygen saturation and total hemoglobulin volume in local skin by near-infrared spectroscopy and its clinical application," International Journal of Biometeorology, vol. 44, Issue 1, pp. 11-19, May 2000.

\* cited by examiner

MONITORING TREATMENT OF PERIPHERAL ARTERY DISEASE (PAD) USING DIFFUSE OPTICAL IMAGING

CROSS REFERENCE TO RELATED APPLICATIONS

This application is a divisional of U.S. application Ser. No. 16/093,775, filed Oct. 15, 2018, which is a US national stage of PCT/US2017/029027, filed Apr. 23, 2017, which claims the benefit of U.S. Provisional Application 62/326,822 filed Apr. 24, 2016, and U.S. provisional application 62/417,741 filed Nov. 4, 2016, each of which is incorporated herein by reference in its entirety.

STATEMENT REGARDING FEDERALLY-SPONSORED RESEARCH

This invention was made with government support under 1R01HL115336-01A1 awarded by NIH-NHLBI. The government has certain rights in the invention.

BACKGROUND

Peripheral arterial disease (PAD) is the narrowing of arteries due to plaque accumulation and in the vascular walls (atherosclerosis). PAD typically manifests itself as claudication, which is defined as a cramping leg pain with ambulation to a set distance. As the disease progresses, this distance becomes progressively shorter, and in later stages the pain becomes severe and present even at rest. Untreated, the disease eventually leads to formation of foot wounds or ulcerations, which can subsequently lead to infection of the wound and tissue loss (gangrene), and ultimately amputation.

PAD affects approximately 12 million individuals in the United States and is associated with significant morbidity and mortality. Every year, PAD is responsible for over 2,750,000 office visits, 10% of which result in hospital admissions. Approximately 45,000 PAD patients die from this disease annually. Furthermore, patients with PAD have an increased risk of stroke and myocardial infarction, and show a two-fold increase in the risk of death from cardiovascular disease. Risk factors for developing PAD include age, smoking, hypertension, hyperlipidemia, hypercholesterolemia, and diabetes.

Patients with severe PAD will often require lower extremity percutaneous transluminal angioplasty or bypass surgery to fix the occluded blood to flow to the extremities. In angioplasty, an empty and collapsed balloon on a guide wire, known as a balloon catheter, is passed into the artery to narrowed locations and then inflated to a fixed size using water pressure. The balloon crushes the fatty deposits, opening up the blood vessel for improved flow; the balloon is then deflated and withdrawn. A stent is then usually placed at the same location to ensure that the vessel remains open. If angioplasty is ineffective, a vascular bypass is conducted. This is very invasive, as the surgeon has to make a large cut and move the muscles and tissue to reach the artery, then re-route it by taking a segment of another artery or using synthetic tubing. Unfortunately, the success of these procedures may not become known until weeks or months after the procedure when either improvements (e.g., healing of an ulcer or remission of symptoms) or no improvements are observed.

SUMMARY OF THE INVENTION

One aspect of the invention is directed to a first apparatus that comprises a first module, a first support structure, a second module, and a second support structure. The first module has a first front surface shaped and dimensioned for contacting a person's skin, and a first plurality of light sources aimed in a forward direction with respect to the first front surface. Each of the first plurality of light sources has a different wavelength. The first module also has a first plurality of light detectors aimed to detect light arriving from in front of the first front surface, and a first plurality of electrical conductors that (a) convey electrical signals that drive the first plurality of light sources and (b) convey electrical signals representative of the light detected by the first plurality of light detectors. The first support structure is shaped and dimensioned to hold the first front surface adjacent to the person's skin at a first position on the person's skin.

The second module has a second front surface shaped and dimensioned for contacting the person's skin, and a second plurality of light sources aimed in a forward direction with respect to the second front surface. Each of the second plurality of light sources has a different wavelength. The second module also has a second plurality of light detectors aimed to detect light arriving from in front of the second front surface, and a second plurality of electrical conductors that (a) convey electrical signals that drive the second plurality of light sources and (b) convey electrical signals representative of the light detected by the second plurality of light detectors. The second support structure is shaped and dimensioned to hold the second front surface adjacent to the person's skin at a second position on the person's skin while the first front surface is being held adjacent to the person's skin at the first position. In this first apparatus, the first position and the second position correspond, respectively, to first and second angiosomes of the person.

In some embodiments of the first apparatus, the first support structure comprises a strap shaped and dimensioned to hold the first front surface adjacent to the person's skin at a calf muscle of the person, and the second support structure comprises a strap shaped and dimensioned to hold the second front surface adjacent to the person's skin on a top portion of a foot of the person.

Some embodiments of the first apparatus further comprise a third module and a third support structure. The third module has a third front surface shaped and dimensioned for contacting the person's skin, and a third plurality of light sources aimed in a forward direction with respect to the third front surface. Each of the third plurality of light sources has a different wavelength. The third module also has a third plurality of light detectors aimed to detect light arriving from in front of the third front surface, and a third plurality of electrical conductors that (a) convey electrical signals that drive the third plurality of light sources and (b) convey electrical signals representative of the light detected by the third plurality of light detectors. The third support structure is shaped and dimensioned to hold the third front surface adjacent to the person's skin at a third position on the person's skin while the first front surface is being held adjacent to the person's skin at the first position and while the second front surface is being held adjacent to the person's skin at the second position. The first position, the second position, and the third position correspond, respectively, to first, second, and third angiosomes of the person.

In some of these embodiments, the first support structure comprises a strap shaped and dimensioned to hold the first front surface adjacent to the person's skin at a calf muscle of the person, and the second support structure comprises a strap shaped and dimensioned to hold the second front surface adjacent to the person's skin on a top portion of a foot of the person. In some of these embodiments, the third support structure comprises a clip shaped and dimensioned to hold the third front surface adjacent to the person's skin on a toe of the person. In some of these embodiments, the third support structure comprises a strap shaped and dimensioned to hold the third front surface adjacent to the person's skin on a bottom portion of the foot of the person.

Optionally, in these embodiments, the strap is shaped and dimensioned to hold the first front surface adjacent to the person's skin at the calf muscle of the person comprises a hook-and-loop fastener, the strap shaped and dimensioned to hold the second front surface adjacent to the person's skin on a top portion of the foot of the person comprises a hook-and-loop fastener, and the strap shaped and dimensioned to hold the third front surface adjacent to the person's skin on a bottom portion of the foot of the person comprises a hook-and-loop fastener.

In some of these embodiments, the strap shaped and dimensioned to hold the first front surface adjacent to the person's skin at the calf muscle of the person comprises a hook-and-loop fastener, and the strap shaped and dimensioned to hold the second front surface adjacent to the person's skin on a top portion of the foot of the person comprises a hook-and-loop fastener.

In some embodiments of the first apparatus, the first support structure and the second support structure are integrated into a single support structure shaped and dimensioned to (i) hold the first front surface adjacent to the person's skin at a calf muscle of the person and (ii) hold the second front surface adjacent to the person's skin on a top portion of a foot of the person. In some of these embodiments, the single support structure is shaped and dimensioned to hold the third front surface adjacent to the person's skin on a bottom portion of the foot of the person.

Some embodiments of the first apparatus further comprise a fourth module that is similar to the first module and a fourth support structure that is similar to the first support structure. These embodiments are configured for placement at four different positions that correspond, respectively, to first, second, third, and fourth angiosomes of the person.

Some embodiments of the first apparatus further comprise at least one processor configured to (a) control generation of the electrical signals that drive the first plurality of light sources, accept data representative of the light detected by the first plurality of light detectors, and determine a first level of perfusion in the first angiosome based on the data representative of the light detected by the first plurality of light detectors; (b) control generation of the electrical signals that drive the second plurality of light sources, accept data representative of the light detected by the second plurality of light detectors, and determine a second level of perfusion in the second angiosome based on the data representative of the light detected by the second plurality of light detectors; and (c) control generation of the electrical signals that drive the third plurality of light sources, accept data representative of the light detected by the third plurality of light detectors, and determine a third level of perfusion in the third angiosome based on the data representative of the light detected by the third plurality of light detectors.

In some of these embodiments, the at least one processor is configured to control generation of a display that simultaneously depicts the first level of perfusion, the second level of perfusion, and the third level of perfusion. In some of these embodiments, the at least one processor is configured to control generation of a display that simultaneously depicts changes in the first level of perfusion over a period of time, changes in the second level of perfusion over the period of time, and changes in the third level of perfusion over the period of time. In some of these embodiments, the at least one processor is configured to control inflation of a pressure cuff during the period of time.

Another aspect of the invention is directed to a first method for monitoring treatment of peripheral artery disease. This method comprises (a) affixing a first plurality of light sources having different wavelengths and a first plurality of light detectors to a first position on a subject's limb, wherein the first position corresponds to a first angiosome of the limb; (b) transmitting light from the first plurality of light sources into the first portion of the subject's limb, detecting light reflected from the first portion of the subject's limb using the first plurality of light detectors, and using diffuse optical imaging to determine a level of perfusion in the first angiosome based on the detected light reflected from the first portion; (c) affixing a second plurality of light sources having different wavelengths and a second plurality of light detectors to a second position on a subject's limb, wherein the second position corresponds to a second angiosome of the limb; and (d) transmitting light from the second plurality of light sources into the second portion of the subject's limb, detecting light reflected from the second portion of the subject's limb using the second plurality of light detectors, and using diffuse optical imaging to determine a level of perfusion in the second angiosome based on the detected light reflected from the second portion. The first plurality of light sources and the first plurality of light detectors remain affixed to the first position during steps (b) and (d), and the second plurality of light sources and the second plurality of light detectors remain affixed to the second position during steps (b) and (d).

Some embodiments of the first method further comprise (e) affixing a third plurality of light sources having different wavelengths and a third plurality of light detectors to a third position on a subject's limb, wherein the third position corresponds to a third angiosome of the limb; and (f) transmitting light from the third plurality of light sources into the third portion of the subject's limb, detecting light reflected from the third portion of the subject's limb using the third plurality of light detectors, and using diffuse optical imaging to determine a level of perfusion in the third angiosome based on the detected light reflected from the third portion. The first plurality of light sources and the first plurality of light detectors remain affixed to the first position during steps (b), (d), and (f), the second plurality of light sources and the second plurality of light detectors remain affixed to the second position during steps (b), (d), and (f), and the third plurality of light sources and the third plurality of light detectors remain affixed to the third position during steps (b), (d), and (f).

In some of these embodiments, steps (b), (d), and (f) are each performed at a first time during which a pressure cuff is not inflated, and steps (b), (d), and (f) are repeated at a second time during which the pressure cuff is inflated.

In some of these embodiments, the first angiosome corresponds to a posterior tibial artery, the second angiosome corresponds to a lateral plantar artery, and the third angiosome corresponds to at least one of an anterior tibial artery and a dorsalis pedis artery.

Some embodiments of the first method further comprise (g) affixing a fourth plurality of light sources having different wavelengths and a fourth plurality of light detectors to a fourth position on a subject's limb, wherein the fourth position corresponds to a fourth angiosome of the limb; and (h) transmitting light from fourth plurality of light sources into the fourth portion of the subject's limb, detecting light reflected from the fourth portion of the subject's limb using the fourth plurality of light detectors, and using diffuse optical imaging to determine a level of perfusion in the fourth angiosome based on the detected light reflected from the fourth portion. The first plurality of light sources and the first plurality of light detectors remain affixed to the first position during steps (b), (d), (f), and (h), the second plurality of light sources and the second plurality of light detectors remain affixed to the second position during steps (b), (d), (f), and (h), the third plurality of light sources and the third plurality of light detectors remain affixed to the third position during steps (b), (d), and (h), and the fourth plurality of light sources and the fourth plurality of light detectors remain affixed to the fourth position during steps (b), (d), (f), and (h).

In some of these embodiments, the first angiosome corresponds to a posterior tibial artery, the second angiosome corresponds to a lateral plantar artery, and the third angiosome corresponds to at least one of an anterior tibial artery and a dorsalis pedis artery. In some of these embodiments, the fourth angiosome corresponds to a medial plantar artery.

In some of these embodiments, steps (b), (d), (f), and (h) are each performed at a first time during which a pressure cuff is not inflated, and steps (b), (d), (f), and (h) are repeated at a second time during which the pressure cuff is inflated.

Another aspect of the invention is directed to a second method of monitoring treatment of peripheral artery disease. This method comprises (a) using diffuse optical imaging to determine a first level of perfusion in each of a plurality of angiosomes of the limb; (b) performing a first surgical intervention to increase perfusion in a first one of the plurality of angiosomes; (c) using diffuse optical imaging to determine a second level of perfusion in each of the plurality of angiosomes after the first surgical intervention; (d) determining if at least one of the second levels of perfusion is indicative of PAD; (e) if a determination is made that at least one of the second levels of perfusion is indicative of PAD, performing a second surgical intervention to increase perfusion in a second one of the plurality of angiosomes; (f) using diffuse optical imaging determine a third level of perfusion in each of the plurality of angiosomes after the second surgical intervention; and (g) determining if the third level of perfusion in the second one of the plurality of angiosomes is still indicative of PAD. At least steps (b)-(g) are performed during a single surgical session.

In some embodiments of the second method, steps (a)-(g) are all performed during the same surgical session.

Some embodiments of the second method further comprise (h) if a determination is made that the third level of perfusion in the second one of the plurality of angiosomes is still indicative of PAD, performing a third surgical intervention to increase perfusion in the second one of the plurality of angiosomes. At least steps (b)-(h) are performed during the same surgical session.

In some embodiments of the second method, the plurality of angiosomes includes an angiosome corresponding to a posterior tibial artery and an angiosome corresponding to a lateral plantar artery. In some of these embodiments, the plurality of angiosomes further includes an angiosome corresponding to at least one of an anterior tibial artery and a dorsalis pedis artery. In some of these embodiments, the plurality of angiosomes further includes an angiosome corresponding to a medial plantar artery.

Another aspect of the invention is directed to a second apparatus. This apparatus comprises a substrate having a front face and a plurality of light sources. Each of the plurality of light sources has a different wavelength, and each of the plurality of light sources is mounted to the substrate. At least a portion of each of the plurality of light sources is disposed in front of the front face. This apparatus also comprises a plurality of light detectors mounted to the substrate, and at least a portion of each of the plurality of light detectors is disposed in front of the front face. This apparatus also comprises a polymer pad shaped and dimensioned to sit in front of the front face having a first plurality of openings shaped and dimensioned to accommodate the at least a portion of each of the plurality of light sources disposed in front of the front face and having a second plurality of openings shaped and dimensioned to accommodate the at least a portion of each of the plurality of light detectors disposed in front of the front face. The polymer pad has a front surface shaped and dimensioned for contacting a person's skin. This apparatus also comprises a plurality of electrical conductors that (a) convey electrical signals that drive the plurality of light sources and (b) convey electrical signals representative of the light detected by the plurality of light detectors. Each of the plurality of light sources is aimed in a forward direction with respect to the front surface of the polymer pad, and each of the plurality of light detectors is aimed to detect light arriving from in front of the front surface of the polymer pad.

In some embodiments of the second apparatus, the polymer pad comprises silicone. Some of these embodiments further comprise a thin transparent polymer sheet disposed on the front surface of the polymer pad. In some of these embodiments, the thin transparent polymer sheet has an adhesive backing. In some of these embodiments, the thin transparent polymer sheet comprises Mylar.

Some embodiments of the second apparatus further comprise a support structure shaped and dimensioned to hold the front surface of the polymer pad adjacent to the person's skin.

Some embodiments of the second apparatus further comprise a strap shaped and dimensioned to hold the front surface of the polymer pad adjacent to the person's skin. Some of these embodiments further comprise a hook-and-loop fastener configured to selectively fasten the strap.

Some embodiments of the second apparatus further comprise a clip shaped and dimensioned to hold the front surface of the polymer pad adjacent to a person's toe.

Another aspect of the invention is directed to a first system that comprises at least two transducers, each having light sources and sinks connected electrically to a processor programmed to generate a time-dependent indication of blood perfusion of respective regions corresponding to each of the at least two transducers. Each of the at least two transducers is configured to releasably attach to a respective one of two separate angiosomes. The processor is programmed to output a time-dependent indication of blood perfusion in real time during a surgical procedure.

In some embodiments of the first system, at least one of the at least two transducers includes a clip that clips on the first toe of a human subject.

In some embodiments of the first system, the angiosomes are in the lower leg of a human subject. In some of these embodiments, one of the at least two transducers is configured to attach to a human calf.

In some embodiments of the first system, the output includes graphs of hemoglobin concentration and time.

The first system may be used to perform the following method: (a) prior to a surgical intervention, applying pressure to a limb to occlude the flow of blood; (b) recording a time-dependent indication of blood perfusion while releasing the pressure; and (c) outputting a result of the recording.

Optionally, in these embodiments, pressure may be applied by a cuff that surrounds the limb. This pressure may optionally be sufficient to cause venous and/or arterial occlusion.

Optionally, these embodiments further comprise, after a surgical intervention, repeating the applying, the recording, and the outputting. Some of these embodiments further comprise performing further surgical intervention based on the data provided by the first and/or second recording.

In some of these embodiments, the method further comprises identifying an artery to be targeted by said intervention responsively to a result of the recording. In some of these embodiments, the surgical intervention includes the restoration of patency in an artery. In some of these embodiments, the restoration includes implantation of a stent.

Another aspect of the invention is directed to a third apparatus for monitoring the blood in a patient's foot. This apparatus comprises a chamber that blocks light, the chamber having a platform sized and shaped to accept a bottom of a patient's foot, the platform having a window that permits light to pass. This apparatus also comprises an illumination source that shines a spot of illumination light on an upper surface of the patient's foot and a controller that controls a position of the spot of illumination on the upper surface of the patient's foot. This apparatus also comprises at least one camera aimed to (a) detect light that originated from the illumination source and was diffusely reflected from an upper surface of the patient's foot and (b) detect light that originated from the illumination source that has passed through the patient's foot. This apparatus also comprises a processor that generates tomographic images from the detected light that was diffusely reflected from the upper surface of the patient's foot and generates tomographic images from the detected light that has passed through the patient's foot.

In some embodiments of the third apparatus, the illumination light comprises laser light that is time series multiplexed. In some of these embodiments, the illumination source comprises a plurality of laser diodes having different wavelengths. In some of these embodiments, the illumination source comprises a 660 nm laser diode and 860 nm laser diode.

In some embodiments of the third apparatus, the position of the spot of illumination is controlled using a 2D galvanometer. In some embodiments of the third apparatus, the light that originated from the illumination source that has passed through the patient's foot is routed to the at least one camera via a window disposed beneath the patient's foot and a plurality of mirrors.

Some embodiments of the third apparatus further comprise a barrier disposed between a path of light that was diffusely reflected from the upper surface of the patient's foot and a path of light that has passed through the patient's foot.

BRIEF DESCRIPTION OF THE DRAWINGS

FIG. 8A shows raw camera images of a solid phantom with an absorber at the top.

FIG. 8B shows raw camera images of a solid phantom with an absorber at the bottom.

FIG. 8C shows raw camera images of a solid phantom with an absorber at the top and bottom.

DESCRIPTION OF THE PREFERRED EMBODIMENTS

SECTION 1: Monitoring Treatment of Peripheral Artery Disease (PAD) Using Diffuse Optical Imaging.

Vascular optical tomographic imaging (VOTI) is an emerging imaging modality capable of detecting hemoglobin concentrations in tissue. VOTI is non-invasive, non-ionizing and does not require contrast injection. In a clinical pilot study involving 40 subject that it has been shown that this technology promises to diagnose peripheral arterial disease (PAD) within lower extremities of diabetic patients with calcified arteries with high sensitivity and specificity.

The VOTI system is capable of quantifying the blood volume changes within the foot during the thigh cuff occlusion and outputting diagnostic parameters, such as change in hemoglobin concentration, enabling the assessment of foot perfusion. VOTI is also capable of providing the locations of under-perfused regions within the foot and evaluating the severity of arterial disease, even within diabetic patients with calcified arteries, who are traditionally difficult to diagnose. M. A. Khalil, et al., Detection of Peripheral Arterial Disease Within the Foot Using Vascular Optical Tomographic Imaging: A Clinical Pilot Study, Eur J Vasc Endovasc Surg. 2015 January; 49(1):83-9.

Using diffuse optical imaging to monitor PAD in multiple locations of the lower extremities during surgical interventions has the potential to objectively assess the success of arterial revascularization. More specifically, assessing the blood flow and resulting tissue oxygenation of multiple locations in parallel in real time during a surgical procedure would considerably improve patient management and could inform the surgeon if the intervention was successful or if additional measures (e.g. stenting a second artery) should be undertaken.

Figure 1A:
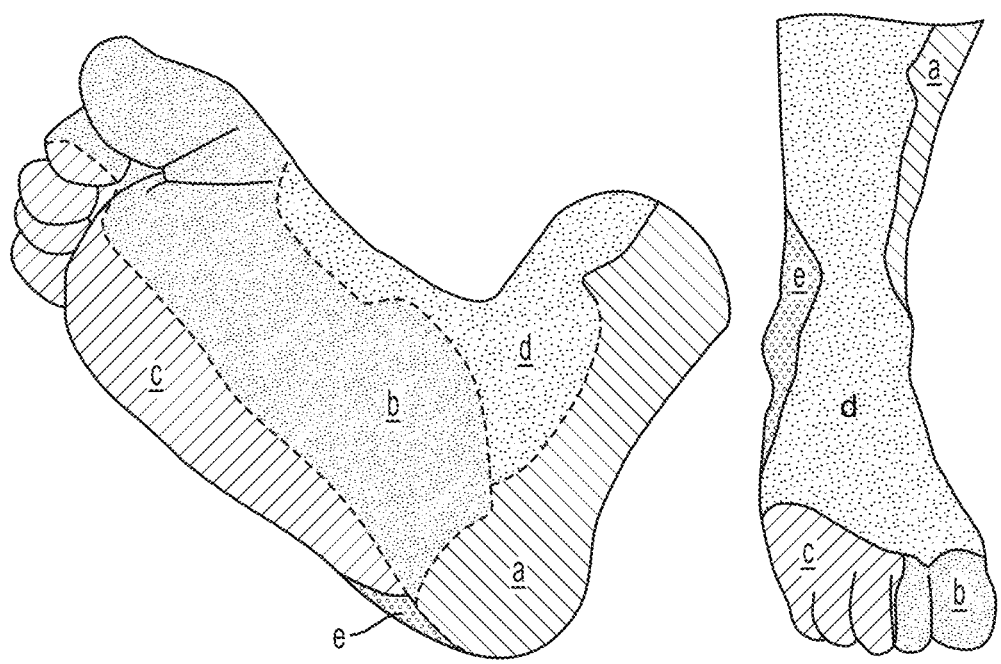
FIG. 1A depicts an angiosome map of a typical leg and foot.

The vascular territories in the legs and feet are called angiosomes. These angiosomes cover distinct three-dimensional blocks of tissue, each of which is fed by one or more distinct source arteries such as the medial sural artery, lateral sural artery, posterior tibial artery (PTA), anterior tibial artery (ATA), and peroneal artery (PA). FIG. 1A is a schematic illustration of a set of such angiosomes in a foot. In this map of angiosomes, region A corresponds to the posterior tibial artery; region B corresponds to the medial plantar artery; region C corresponds to the lateral plantar artery; region D corresponds to both the anterior tibial artery and the dorsalis pedis artery; and region E corresponds to the peroneal artery.

In PAD patients, vessels within certain angiosomes can be affected to a larger degree than others, depending on the location of the blockage the patient is suffering from further upstream. For example, while a blockage in the femoral artery may affect perfusion in the entire foot, a blockage in the anterior tibial artery will affect perfusion in the arcuate artery more so than the posterior tibial artery would.

The embodiments described herein can take advantage of the angiosome configuration of the lower legs and feet to help identify the origin of various problems (e.g., ulcerations). The embodiments described herein can also be used to help surgeons choose whether a bypass or an endovascular procedure has the best chance of healing an existent ischemic ulcer. In addition, monitoring the multiple angiosomes in parallel may provide valuable feedback to the surgeon as to the efficacy of the revascularization to the ulcers. In addition, using multiple channels can provide increased sensitivity of the vascular changes, which can lead to a more accurate monitor of hemoglobin concentration changes.

Figure 1B:
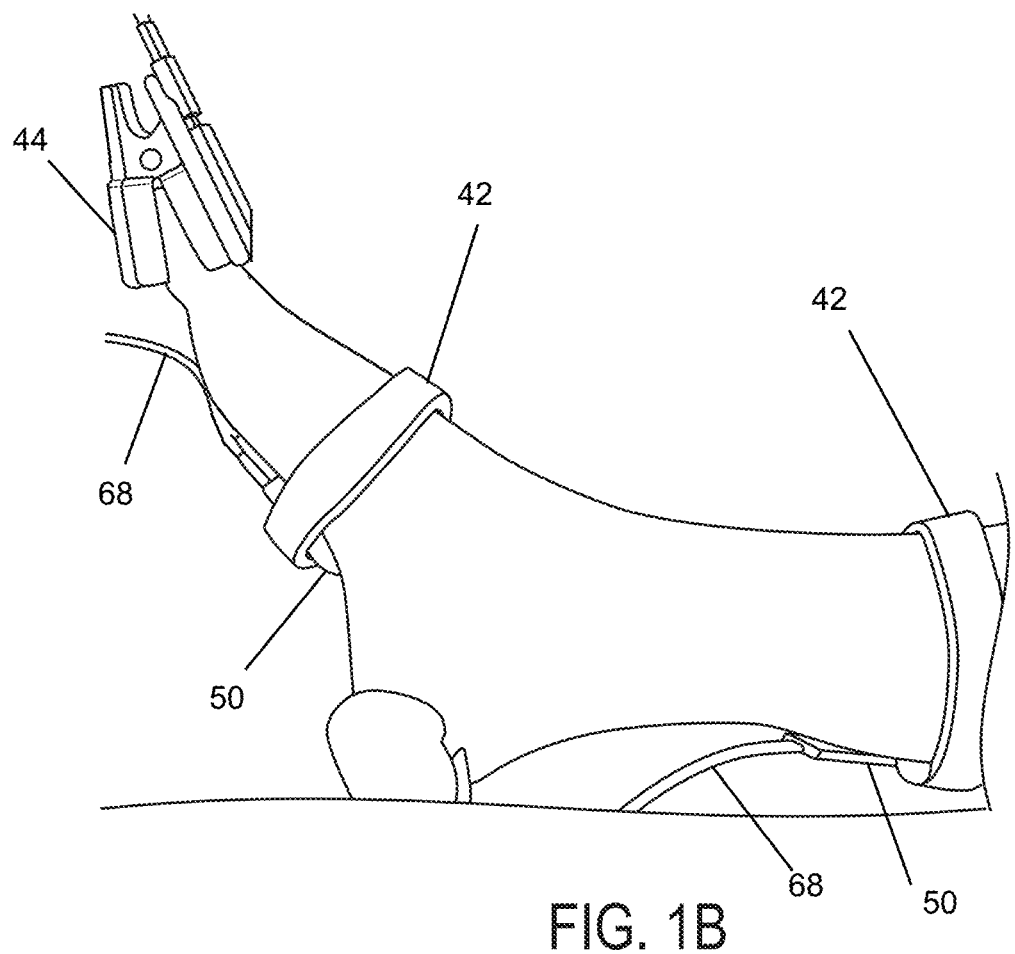
FIG. 1B depicts positioning a patch or module on a plurality of those angiosomes.

FIG. 1B depicts an embodiment configured to simultaneously monitor the perfusion in a plurality of angiosomes using a plurality of interface modules 50, each of which is held up against a subject's body at a different position that corresponds to a respective angiosome. In the illustrated example, one of the modules 50 is held up against the calf muscle (which corresponds to the posterior tibial artery) by a strap 42; one of the modules 50 is held up against the outer bottom of the foot (which corresponds to the lateral plantar artery) by a strap 42; and one of the modules 50 is held against the subject's toe (which corresponds to the medial plantar artery) by a clip 44.

Figure 2:
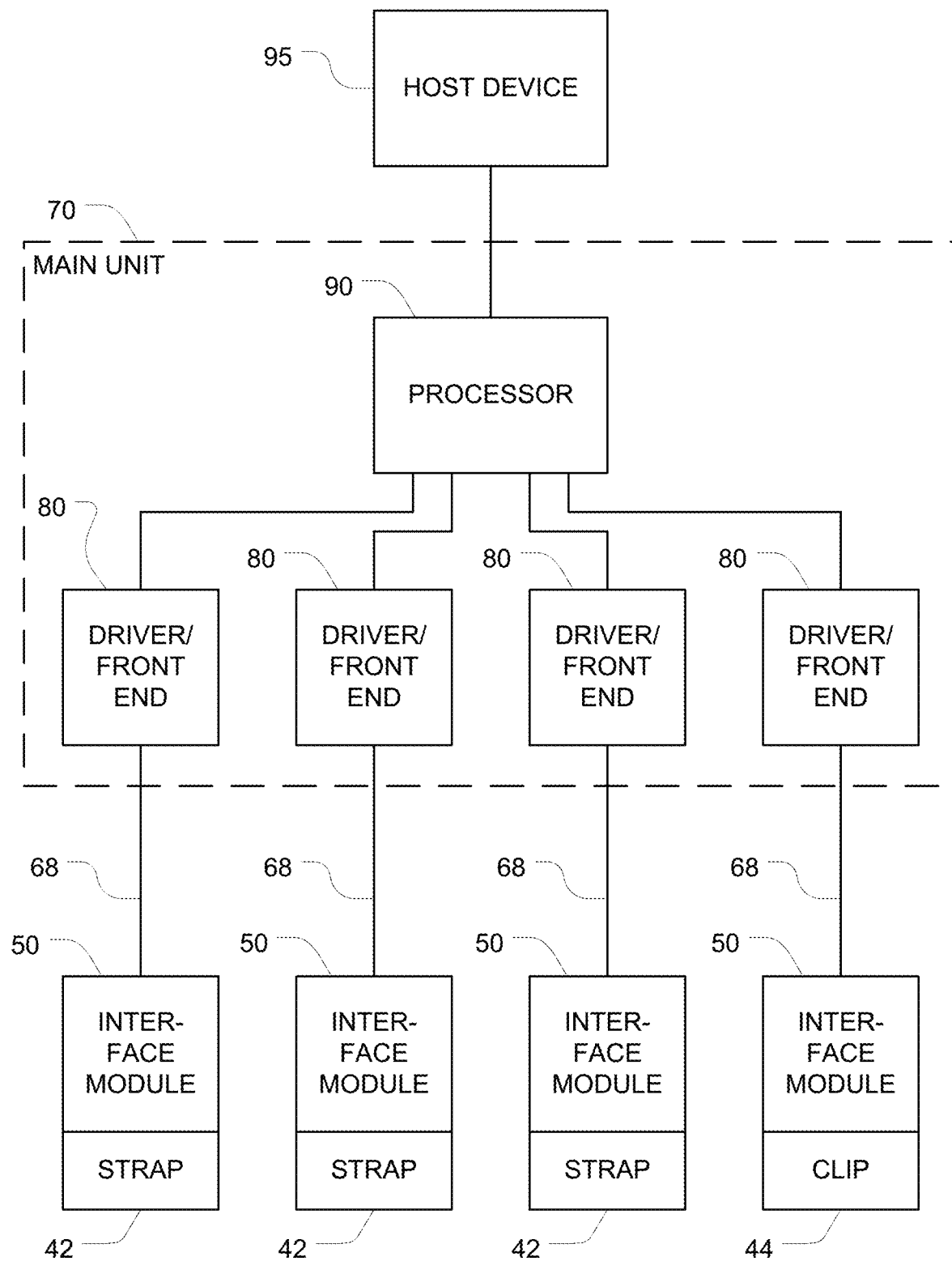
FIG. 2 is a block diagram of an embodiment that monitors the perfusion in a plurality of locations, each of which preferably corresponds to a different angiosome.

FIG. 2 is a block diagram of one embodiment that monitors the perfusion in a plurality of locations, each of which preferably corresponds to a different angiosome. This embodiment includes a plurality of interface modules 50 (also referred to herein as interface patches). The interface patches 50 are placed in multiple places on the foot and calf where perfusion is likely to be affected by the surgical intervention (e.g., the regions depicted in FIG. 1). Preferably, the patches are positioned so that each patch corresponds to a different angiosome.

Each of the interface patches 50 includes a plurality of light sources and light detectors. These light sources shine deep red or near-infrared light into the body part under investigation. That light is absorbed and scattered by the body, and any light emitted is collected by light detectors that are in contact with the body surface. Each of the interfaces patches 50 is connected to a corresponding driver/front end subsystem 80 that is responsible for driving the light sources in the interface patches 50 and acting as a front end for the light detectors in the interface patches 50. Data representing the detected light is then forwarded from the driver/front end subsystems 80 to a processor 90. This data is then used to generate maps of the changes in the concentrations of oxy-hemoglobin [HbO$_2$], deoxy-hemoglobin [Hb], and total hemoglobin [THb]=[HbO$_2$]+[Hb], in the region corresponding to each of the plurality of interface patches 50. In addition, other tissue parameters, such as oxygen saturation StO$_2$=[HbO$_2$]/[THb], water concentration [H$_2$O], tissue scattering $\mu_s$ could also be derived.

Traces and maps of these parameters can then be displayed in real time on a monitor that the surgeon can view during the intervention. A monitor (not shown) may be integrated into the main unit 70. Alternatively, the monitor may be associated with a host device 95 that accepts data from the main unit 70 and displays that data.

Note that while the embodiment illustrated in FIG. 2 depicts four patches 50 and four corresponding data channels through the driver/front end subsystems 80, a different number of patches and corresponding channels may be used. For example, in some embodiments there will only be two or three patches 50 and a corresponding number of channels. In alternative embodiments, there may be more than four patches (e.g. between 5 and 8) and a corresponding number of channels.

The FIG. 2 embodiment may be used for intraoperative monitoring during vascular surgery to improve the efficacy of arterial revascularization for patients suffering from PAD. The design permits surgeons to view changes during surgery and to help determine the efficacy of revascularization procedures.

Figure 3A:
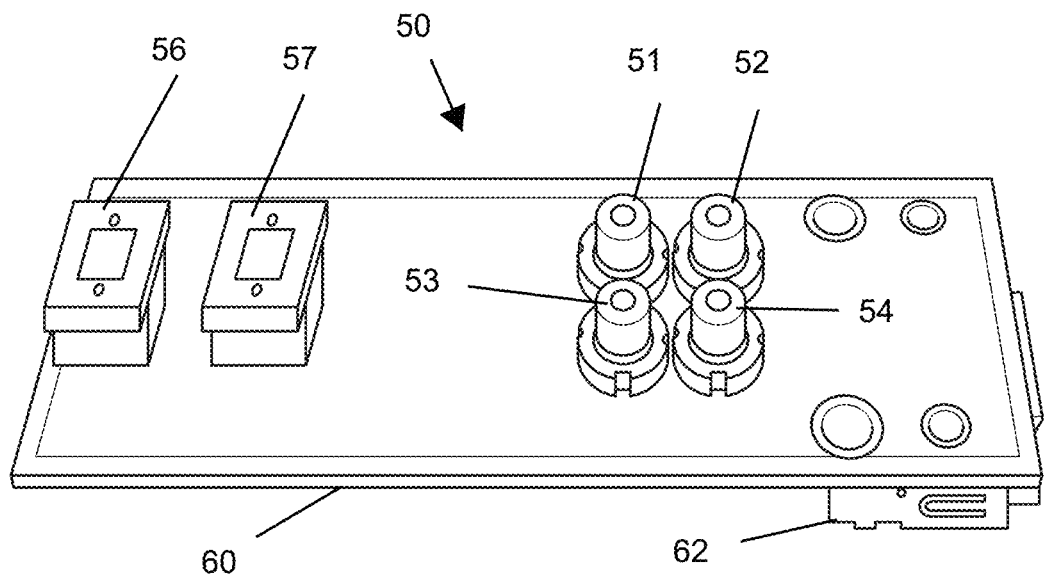
FIG. 3A depicts an example of an interface patch for the FIG. 2 embodiment.

FIG. 3A depicts an example of an interface patch 50. In this example, a plurality of light sources (e.g., laser diodes 51-54) and a plurality of photodetectors (e.g., photodiodes 56, 57) are mounted on a printed circuit board 60 with their bodies disposed in front of the front face of the PCB 60. The PCB 60 is preferably rigid. A suitable size for the PCB is 3×2 cm. In this embodiment, each patch 50 contains four laser diodes 51-54, each having a different wavelength (e.g. in the 670-905 nm range). Each patch 50 also contains two photodiodes 56, 57. In some embodiments, the distances between the sources and the detectors range between 10-25 mm (depending on which source and which detector is used as an endpoint).

In some embodiments, the laser diodes 51-54 are 5 mW 5.6 mm-diameter laser diodes (e.g., from Thorlabs) at wavelengths of 674 nm, 780 nm, 808 nm, and 850 nm, respectively. In alternative embodiments, a different set of wavelengths (e.g., 780 nm, 808 nm, 850 nm, and 904 nm) may be used. These wavelengths provide a range of spectral information to reconstruct the absorption coefficient, the reduced scattering coefficient, oxygenated hemoglobin ([HbO2]), and deoxygenated hemoglobin ([Hb]) while working within the limited selection of wavelengths commercially available in this small package.

Light from these laser diodes passes through the tissue that is disposed in front of the interface patch 50 and is absorbed and scattered. A portion of that light is back-reflected to two photodiodes 56, 57. In some preferred embodiments, the photodiodes are Hamamatsu S1337-33BR silicon photodiodes (SiPD). Preferably the light sources and photodetectors are positioned on the PCB to provide precise source-detector distances. In the illustrated example, these distances are between 9-19 mm (for photodiode 57) and between 15-25 mm (for photodiode 56).

Each patch also has a plurality of electrical conductors (not shown) that (a) convey electrical signals that drive the laser diodes 51-54 from a connector 62 to those laser diodes and (b) convey electrical signals representative of the light detected by the photodiodes 56-57 from the connector 62 to those photodiodes.

Figure 3B:
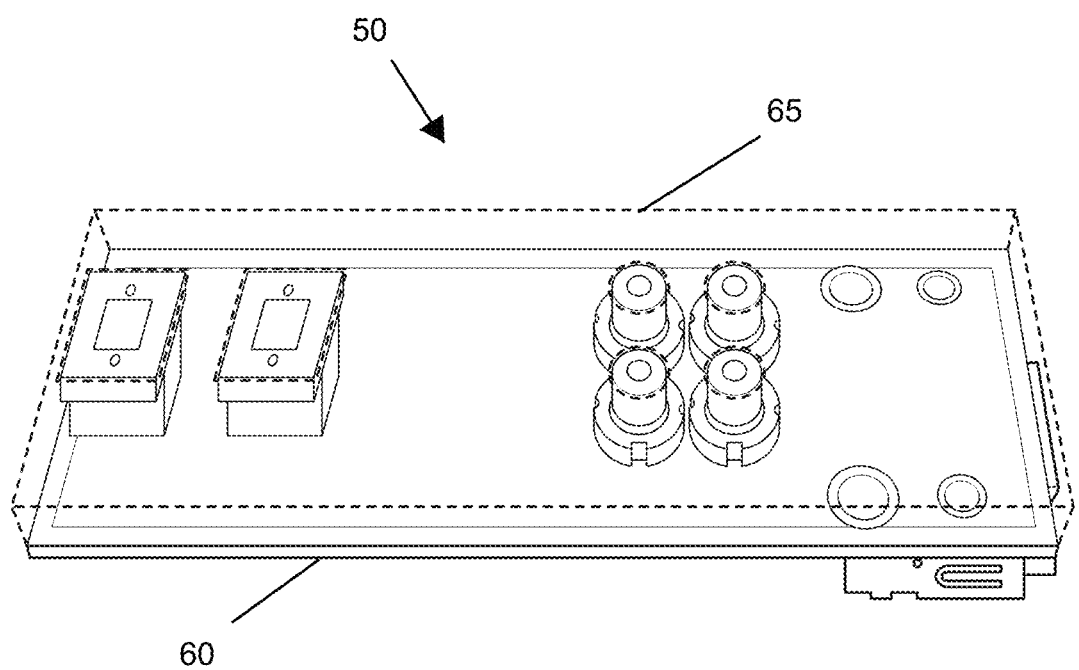
FIG. 3B depicts the FIG. 3A interface patch with its polymer pad attached.

Turning now to FIG. 3B, in some embodiments, a polymer pad 65 sits in front of the front face of the PCB 60. The rear surface of the polymer pad 65 is preferably flush with the front face of the PCB 60. The polymer pad 65 has a plurality of close-fitting cut-outs or openings shaped and dimensioned to accommodate the portion of each of the plurality of light sources that is disposed in front of the front face of the PCB 60. The polymer pad 65 also has a plurality of close-fitting cut-outs or openings shaped and dimensioned to accommodate the portion of each of the plurality of light detectors that is disposed in front of the front face of the PCB 60. The result is a relatively smooth front surface that is either flush or very close to flush with the tops of the laser diodes 51-54 and the tops of the photodiodes 56, 57.

The laser diodes 51-54 are aimed in a forward direction with respect to the front surface of the polymer pad 65, and the photodiodes 56-57 are aimed to detect light arriving from in front of that front surface. The end result is a configuration that provides for comfortable placement against a person's skin with the optical components 51-57 flush with the tissue surface, so that light from the laser diodes 51-54 can shine into the person's body and so that light reflected back from the person's body can be detected by the photodiodes 56, 57.

In some embodiments, the polymer pad 65 is made of silicone. In these embodiments, the polymer pad 65 may be formed using a suitably shaped mold. A silicone mixture is poured into the mold and removed. The mold can be reused to create multiple copies of the polymer pad 65.

Optionally, an adhesive layer may be added to the front surface of the polymer pad 65 such that it will stick to the patient's foot for several hours. A double-sided adhesive strip or an adhesive layer may be placed on top of the silicone mold to act as this adhesive. Once the operation is complete, the silicone interface can be discarded, making the rest of the patch 50.

Optionally, a thin transparent polymer sheet (e.g., Mylar) may be disposed over the front surface of the polymer pad to and over the optical components 51-57 to protect those components from contamination and/or getting dirty. An adhesive backing may be used to adhere the thin transparent polymer sheet to the polymer pad 65, and an adhesive may be applied to the front face of the thin transparent polymer sheet so that it will adhere to the patient's skin.

Each of the interface patches 50 is preferably non-intrusive, lightweight, and durable. Each patch 50 preferably has an associated support structure shaped and dimensioned to hold the front surface of the polymer pad 65 adjacent to the person's skin at a particular position on the person's skin that corresponds to a respective angiosome. In those embodiments that include a transparent polymer sheet, the transparent polymer sheet will be interposed between the polymer pad 65 and the person's skin while the polymer pad 65 is being held adjacent to the person's skin.

Returning to FIG. 1B, in some embodiments, this support structure comprises a strap 42. Optionally, this strap 42 may be fastened in place by a hook-and-loop fastener (e.g. Velcro®). The length and thickness of the strap 42 will depend on the anatomical location at which it will be used. To use these embodiments, the patch 50 is positioned adjacent to the person's skin, and the strap 42 is fastened at a position that gently squeezes the patch 50 against the person's skin so that the optical components on the patch 50 can effectively transmit light into the person's body and receive light reflected back from the person's body. The strap 42 may be configured and oriented so that it does not interfere with the cables 68 that terminate on the patch 50.

In some embodiments, a single strap 42 may be relied on to secure two or more patches 50 in position adjacent to the person's skin. For example, a single strap that wraps around the midportion of a person's foot can be used to secure one patch 50 adjacent to the top portion of the foot and a second patch 50 adjacent to the sole of the person's foot.

In some embodiments, the support structure comprises a clip 44, which may be similar in construction to the toe clips and the finger clips that are commonly used in commercially available pulse oximetry systems. To use these embodiments, the clip 44 is opened by squeezing it, the patch 50 is positioned with the front surface of the polymer pad 65 adjacent to the person's skin at the desired location on the person's body (e.g. the toe) and the clip 44 is released. The clip 44 gently squeezes the patch 50 against the person's toe so that the optical components 51-57 can effectively transmit light into the person's body and receive light reflected back from the person's body. The clip 44 is preferably configured and oriented so that it does not interfere with the cables 68 that terminate on the patch 50.

The use of the toe clips 44 in combination with the straps 42 make it easy to monitor the perfusion of multiple angiosomes in parallel in a convenient and comfortable manner. For example, a first strap 42 can secure one patch 50 to the top of the foot and a second patch 50 to the sole of the foot; a second strap 42 can secure a third patch to the calf muscle; and a clip 44 can secure a fourth patch to the big toe.

In alternative embodiments, all the support structures are integrated into a single sock-like support structure shaped and dimensioned to (i) hold the first front surface adjacent to the person's skin at a calf muscle of the person and (ii) hold the second front surface adjacent to the person's skin on a top portion of a foot of the person. Optionally, this single support structure is shaped and dimensioned to hold the third front surface adjacent to the person's skin on a bottom portion of the foot of the person.

Returning to FIG. 2, the driver/front end subsystem 80 drives the laser diodes, receives signals from the photodiodes in the patches 50 discussed above in connection with FIG. 3, and perform the initial processing steps on those incoming signals.

Note that in the FIG. 2 embodiment, there are four system channels, and each of those channels uses four different deep red or near-infrared wavelengths of light to illuminate tissue. Each channel includes one patch 50 and each patch 50 has a corresponding driver/front end subsystem 80. Appropriate cables 68 connect the optical components 51-57 on the interface patches 50 to the respective driver/front end subsystem 80. For example, a cable 68 that contains 15 leads may be used to operate each patch and provides electrical isolation to prevent noise from being introduced. This cable may include, for example, eight conductors for interfacing with the four lasers, four conductors for interfacing with the two photodiodes, and three conductors for shielding. The length of the cables 68 should be appropriate for the anatomic location at which it will be used, and will typically be on the order of 1 m long.

A variety of alternative embodiments for implementing the driver/front end subsystem 80 can be readily envisioned. One such alternative is described in U.S. application Ser. No. 14/348,081, which published as US2014/0243681 and is incorporated herein by reference in its entirety.

Figure 4:
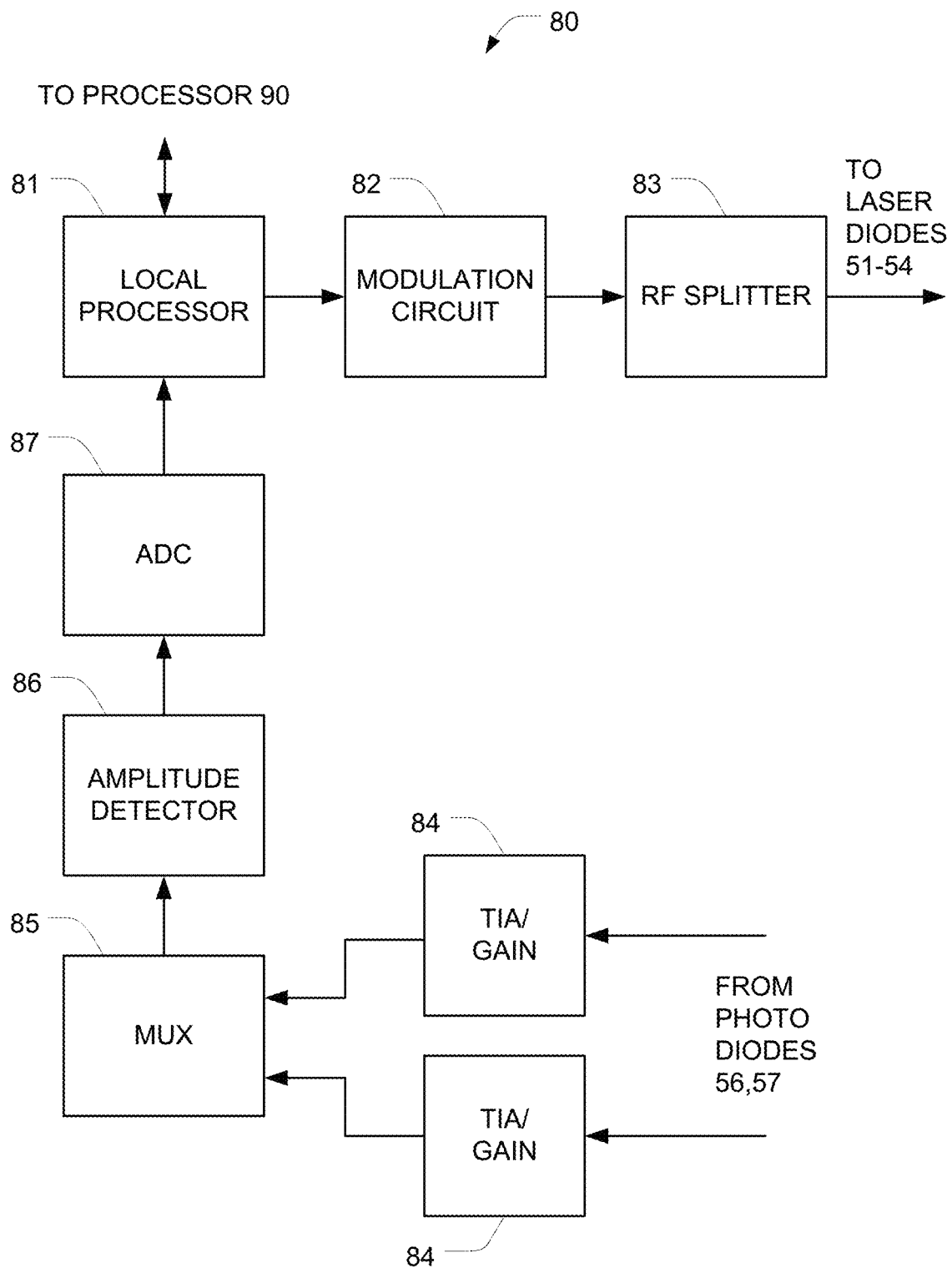
FIG. 4 is a block diagram driver/front end subsystem of the FIG. 2 embodiment.

FIG. 4 is a block diagram of another embodiment of a driver/front end subsystem 80 that may be used to drive the laser diodes and receive signals from the photodiodes in the patches 50 discussed above in connection with FIGS. 2 and 3. In this embodiment, a microcontroller 81 accepts instructions from the processor 90 (shown in FIG. 2) and acquires data according to the scanning profile. Modulation signals control the output power of the lasers and is also used for signal mixing for I/Q detection. Quadrature detection is sampled through an ADC 87 and the microcontroller 81 computes the amplitude of the detected signal.

As for the driver portion of the subsystem 80, the laser source for each wavelength may be modulated programmatically at, for example, 5 kHz using a combination of a 1 kHz-33 MHz Oscillator (LTC69034, Linear Technology), a binary counter (M74HC4820, STMicroelectronics) and a low-pass filter (LTC1067, Linear Technology). The modulation of the input light provides advantages over non-modulated light including superior noise rejection (including ambient light) as well as the ability to illuminate the tissue simultaneously with multiple wavelengths. The modulation circuit 82 uses an RF splitter 83 so that the modulated signal is routed to the driver with the same amplitude and phase. Each laser driver is preferably designed with the ability to trim the power of laser light to maximize laser power and control for easy precise calibration of laser light.

In some embodiments, all four laser modulation frequencies are, selectably, acquired simultaneously. Modulation channels drive the laser diodes and an RF switch controls where the modulation signal is routed. This configuration can increase laser power and permit precise calibration of laser light.

The front end portion of the subsystem 80 uses a pair of transimpedance amplifiers 84 (i.e. one for each of the photodiodes on the corresponding interface patch 50 (shown in FIG. 2). Current from those photodiodes is converted to voltage by the transimpedance amplifiers 84 that optionally utilize a bandwidth-extension technique to extends the bandwidth of the circuit at higher gain settings. The signal may be further amplified using a programmable gain amplifier (PGA) stage to optimize the signal to the scale range of the ADC 87. This chip also uses a biasing circuit to offset the voltage to the center voltage to maximize the dynamic range of the detection subsystem.

After amplification, a filter with a cutoff frequency of, for example, 10 kHz is preferably used to remove noise from the signal. A wide variety of filters are suitable for this purpose, such as first-order passive low-pass filters, fourth order lowpass Butterworth filters, and tenth order low-pass filters implemented using a programmable filter stage such as the LTC1569-7. Using the latter of these filters can advantageously improve the signal as demodulation of the signal can be noise dependent. In addition, gain control of the PGA and the cutoff frequency of the filter stage can also be set via the microcontroller 81 and their values can be adjusted through an appropriate user interface.

Once the signals from both channels are conditioned using any of these approaches, they are multiplexed by multiplexer 85. A logarithmic detector 86 may then be used for amplitude detection. This may be used to help compute the detected signal amplitude but not the phase. Computing the logarithmic equivalent may also provide compression of the voltage signal so demodulation is not required. The output of the detector is a voltage with a scaling on the order of between 10 and 50 mV/dB (e.g. 15 or 30 mV/dB), which may be sampled by a 16-bit ADC 87 (e.g. the LTC6910 or LTC1865) at appropriate speeds (e.g. between 10 kHz and 150 kHz). Many samples may be acquired and averaged to produce one value representing the amplitude of the acquired signal.

In some embodiments, the front end portion of the subsystem 80 may use oversampling regardless of the modulation frequency range (e.g., at 0-5 kHz). A discrete anti-aliasing filter may be used instead of an integrated circuit. A dedicated logarithmic detector may be used for amplitude detection. The unit may be used to help compute the detected signal amplitude but not the phase. Optionally, a dedicated IC may be used to improve the speed of each channel. Computing the logarithmic equivalent may provide compression of the voltage signal so demodulation is not required within the microprocessor 81. Optionally, many samples may be acquired and averaged to produce one value representing the amplitude of the acquired signal.

Returning to FIG. 2, the processor 90 receives data from each of the driver/front end subsystems 80, and sends instructions to those subsystems 80 to control various parameters related to driving the laser diodes and detecting signals from the photodetectors. A variety of alternative embodiments for implementing the processor 90 and the program that it executes can be readily envisioned. One such alternative is described in U.S. application Ser. No. 14/348,081, which published as US2014/0243681 and is incorporated herein by reference in its entirety.

Alternatively, the processor 90 may receive data from each of the driver/front end subsystems 80, and send instructions to those subsystems 80 as follows. A suitable DSP/microcontroller may be used as the processor 90. One example is the PIC32MX695F512H by Microchip Technologies, which provides both USB connectivity and DSP functionality. Digital control may be provided of the source and detector stages as well as peripherals. The signals may be demodulated using digital lock-in detection. In some embodiments, demodulation of all four wavelengths for each channel is implemented in one imaging cycle, providing the ability to illuminate at source lasers at once. This increases the scan rate of the system. With the speed and DSP functionality of the microcontroller 90, the speed of the system can be about 12 Hz for no combination of illumination, about 18 Hz for two combined wavelengths, and about 24 Hz when all sources are illuminated. Demodulation may be implemented in the processor 90. In alternative embodiments, demodulation may be assisted or performed locally in each of the driver/end subsystems 80 by the respective local microcontrollers 81 (shown in FIG. 4). Once demodulated, the processor 90 passes the resulting data back (e.g., via Bluetooth or USB) to the host controller 95.

A firmware routine in the processor 90 may be used to measure the optimal gain setting for the PGA for a given sample. While the probe is at the sample, a gain optimization routine may illuminate all of the lasers at all of the gain settings. The best gain may be chosen for each source detector pair by computing the highest amplitude of the signal without saturation.

Reconstruction algorithms are used to compute the special distributions of $\mu_a$, $\mu_s'$, and the concentrations of oxygenated hemoglobin ([HbO2]), and deoxygenated hemoglobin ([Hb]). Examples of suitable algorithms can be found in US2014/0243681, which is incorporated herein by reference.

In some embodiments, the diffuse spectroscopic technique is based on the reflectance measured at multiple locations on the surface of the medium, where the diffuse reflectance depends solely on the absorption coefficient $\mu_a$ and the reduced scattering coefficient $\mu'_s$ and the source-detector separation d. Under the assumption of a semi-infinite homogeneous medium, the closed-form analytic solution for the spatially resolved reflectance is given by $$R(d)_{dc} = \frac{1}{4\pi\mu'_t}\left[\left(\mu_{eff} + \frac{1}{r_1^2}\right)\frac{\exp(-\mu_{eff}r_1)}{r_1^2} + \left(\frac{4}{3}A + 1\right)\left(\mu_{eff} + \frac{1}{r_2}\right)\frac{\exp(-\mu_{eff}r_2)}{r_2^2}\right], \quad (1)$$

where $$r_1 = \sqrt{\left(\frac{1}{\mu'_t}\right)^2 + d^2}, \quad r_2 = \sqrt{\left[\frac{\frac{3}{4}A + 1}{\mu'_t}\right]^2 + d^2} \quad (2)$$

Here $\mu_{eff}$ is the effective attenuation coefficient $\mu_{eff} = \sqrt{3\mu_a\mu'_t}$, $\mu'_t$ is the total transport coefficient ($\mu'_t = \mu_a + \mu'_s$) and A is the internal reflection parameter that takes into account the refractive index mismatch at air-tissue interface.

A multispectral direct method exploits the following relations that describe the tissue absorption, chromophore concentration, and scattering as $$\mu_a(\lambda) = \Sigma_{i=1}^{N_c}\varepsilon_i(\lambda)C_i, \quad (3)$$

and, $$\mu'_s = A\lambda^{-b} \quad (4)$$

where $\varepsilon_i(\lambda)$ and $C_i$ are the absorption extinction coefficient and the concentration for the ith chromophore in tissue. Nc is the number of tissue chromophores that contribute to the absorption at wavelength $\lambda$. The scattering parameters A and b are the scattering amplitude and the scattering power, respectively. The multispectral direct method reconstructs Ci, A, and b.

The SRS problem with the direct approach can be formulated as the following inverse problem where the optimal solution can be found by minimizing the misfit between predictions Rd and measurements zd of the reflectance on the tissue surface $$F(x) = \Sigma_{\lambda, d}(R_d^\lambda - z_d^\lambda)^2, \quad (5)$$

where x is the vector of all unknowns, e.g., x=($C_j$, A, b). To minimize this equation, an evolution strategy algorithm may be implemented.

The host device 95 may communicate with the main unit 70 using any of a wide variety of suitable user interfaces. One example of such a user interface is a MATLAB based graphical user interface (GUI). The GUI is able to control the experimental parameters of the system, start and stop data from being acquired, and save data to files. The GUI from the host device 95 communicates directly with the processor 90 of the main unit 70. The processor 90 processes the parameter commands from the host device 95 and controls the driver/front end subsystems 80 and their data flow back through the processor 90. The processor 90 also can manage power for the entire system.

The GUI can also be used to select the channels to be used in the experiment and enter the appropriate settings for each channel. If the patches 50 are attached to the subject, the GUI can adjust the settings using a calibration scheme. The user can save and load the settings, if needed for a patient profile.

Examples of the functionality that may be provided via the host device 95 include, but are not limited to: (a) file name saving and loading options for user settings; (b) selection of channels used for experiments and radio buttons for channel settings; (c) gain settings for each source detector pair of the channel; (d) experimental call functions that connect to the device, download settings, and calibrate the system; (e) experiment start and stop buttons; and (f) data display of the user selected channel or channels.

Once the settings are downloaded to the system, the user can start the experiment. The incoming data from the system is parsed by channel and is stored to file. The user can also view the data stream for a particular channel during the experiment.

In some embodiments, the processor 90 is used to process the parameter commands from the host device 95 and control the driver/front end subsystems 80 and their data flow through the processor 90. The processor 90 may include a DSP that controls the timing of acquisition of the various channels, communication circuitry that makes it possible to communicate with the host 95 (e.g., via a serial datalink or Bluetooth), a USB connection for power and communication. Once commands are received from the host device 95, the processor 90 may parse the experimental settings and execute the imaging sequence by sending commands to the appropriate driver/front end subsystems 80 for imaging. Data sent back to the processor 90 from those subsystems 80 are packaged and sent to the host device 95.

In some embodiments, the host device 95 can use a Labview interface and an Android mobile application. The mobile application controls the hardware and receives and stores the transmitted data. The Android SDK provided the tools and API's necessary to communicate with the hardware via Bluetooth. A terminal emulator may be used to communicate with the main unit 70 using, e.g., a Bluetooth serial adapter. The application running on the host device 95 allows the user to control the hardware (initialize the device, start recording, and stop recording) using buttons in the interface that send unique commands to the main unit 70. The application also allows the user to connect and disconnect to a paired Bluetooth device through a menu. In separate threads, the data is parsed, stored on the devices removable SD storage, and plotted in real-time to on-screen graphs.

In some embodiments, a Labview PC GUI running on the host device 95 is used where real-time algorithmic processing is needed, or when long experimentation times make USB connectivity between the host device 95 and the main unit 70 more suitable. At startup, the Labview GUI can automatically connect to the main unit 70. The GUI controls the device using the same commands as the Android application, and data received by the Labview GUI is saved to a user specified location. The user also has the ability to run the reconstruction algorithm in real time, to measure absorption, reduced scattering, as well as concentrations of oxy- and deoxy-hemoglobin.

Optionally, additional peripherals such as a 3-axis accelerometer may be to help the user in positioning and steadiness where needed. This option may be valuable for dynamic measurements where an unsteady subject could cause motion artifacts.

The apparatus described above in connection with FIGS. 1-4 may be used to perform a first method for monitoring treatment of peripheral artery disease. This method comprises (a) affixing a first plurality of light sources having different wavelengths and a first plurality of light detectors to a first position on a subject's limb, wherein the first position corresponds to a first angiosome of the limb; (b) transmitting light from the first plurality of light sources into the first portion of the subject's limb, detecting light reflected from the first portion of the subject's limb using the first plurality of light detectors, and using diffuse optical imaging to determine a level of perfusion in the first angiosome based on the detected light reflected from the first portion; (c) affixing a second plurality of light sources having different wavelengths and a second plurality of light detectors to a second position on a subject's limb, wherein the second position corresponds to a second angiosome of the limb; and (d) transmitting light from the second plurality of light sources into the second portion of the subject's limb, detecting light reflected from the second portion of the subject's limb using the second plurality of light detectors, and using diffuse optical imaging to determine a level of perfusion in the second angiosome based on the detected light reflected from the second portion. The first plurality of light sources and the first plurality of light detectors remain affixed to the first position during steps (b) and (d), and the second plurality of light sources and the second plurality of light detectors remain affixed to the second position during steps (b) and (d).

Some embodiments of the first method further comprise (e) affixing a third plurality of light sources having different wavelengths and a third plurality of light detectors to a third position on a subject's limb, wherein the third position corresponds to a third angiosome of the limb; and (f) transmitting light from the third plurality of light sources into the third portion of the subject's limb, detecting light reflected from the third portion of the subject's limb using the third plurality of light detectors, and using diffuse optical imaging to determine a level of perfusion in the third angiosome based on the detected light reflected from the third portion. The first plurality of light sources and the first plurality of light detectors remain affixed to the first position during steps (b), (d), and (f), the second plurality of light sources and the second plurality of light detectors remain affixed to the second position during steps (b), (d), and (f), and the third plurality of light sources and the third plurality of light detectors remain affixed to the third position during steps (b), (d), and (f).

In some of these embodiments, steps (b), (d), and (f) are each performed at a first time during which a pressure cuff is not inflated, and steps (b), (d), and (f) are repeated at a second time during which the pressure cuff is inflated. This permits the surgeon to ascertain how the pressure impacts the perfusion.

Figure 5E:
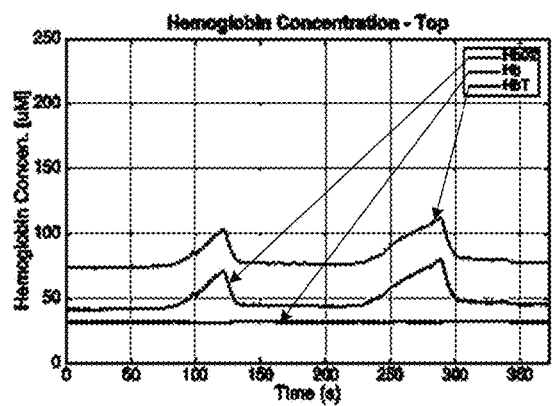
FIGS. 5A, 5C, and 5E are displays of perfusion over time in the a, c, and e angiosomes prior to an intervention.
Figure 5C:
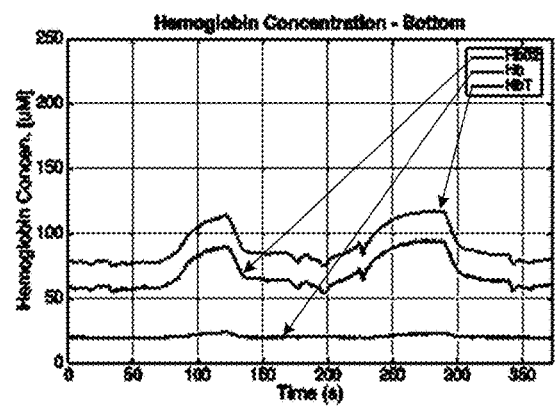
Figure 5A:
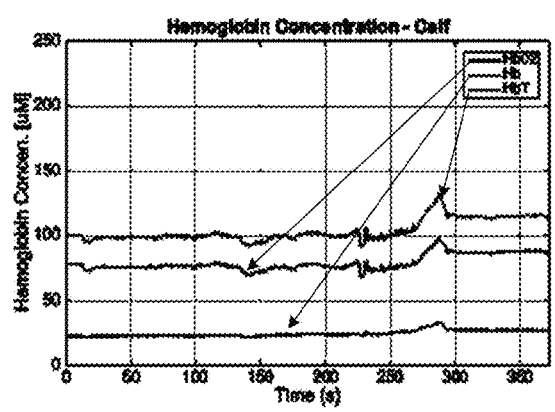

FIGS. 5A, 5C, and 5E depict displays of perfusion/hemoglobin concentration over a 6.5 min interval of time that are simultaneously presented to the surgeon prior to an intervention under control of the processor 90 or the host device 95. This interval of time includes two 1-minute cuff inflations—one at 60 mmHg and one at 100 mmHg. In the illustrated example, the display for angiosome c (lateral plantar artery) appears normally perfused; the display for angiosome e (peroneal artery) is somewhat compromised (note the non-rounded peaks); and the display for angiosome a (posterior tibial artery) shows almost no response indicating poor perfusion.

Figure 6E:
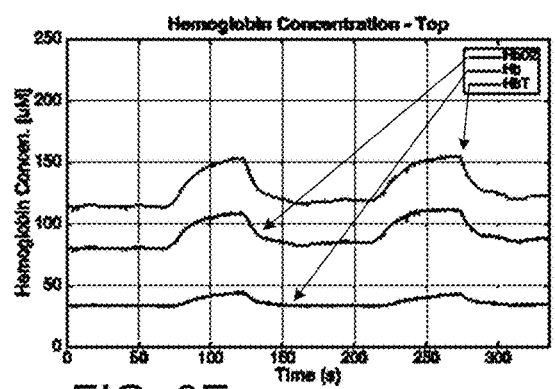
FIGS. 6A, 6C, and 6E are displays of perfusion over time in the a, c, and e angiosomes subsequent to the intervention.
Figure 6C:
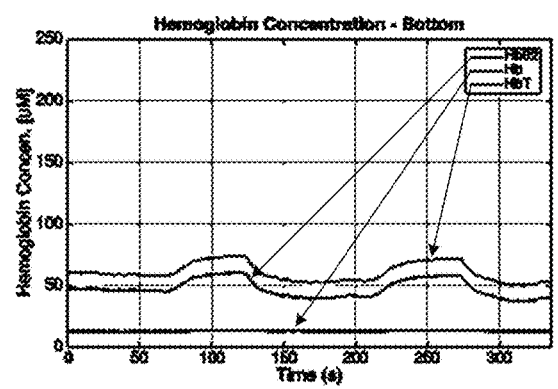
Figure 6A:
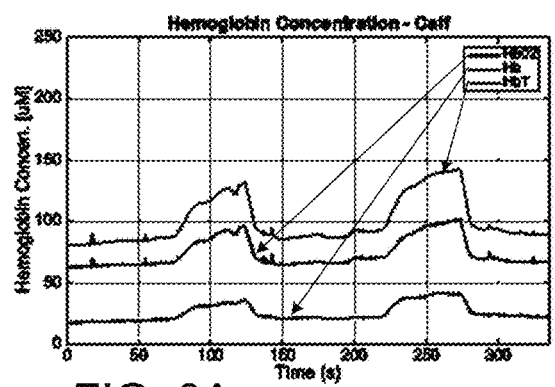

FIGS. 6A, 6C, and 6E depict displays of perfusion/hemoglobin concentration over a second 6.5 min interval of time that are simultaneously presented to the surgeon after placing a stent in the posterior tibial artery to address the problem in angiosome a noted in the previous paragraph. This interval of time also includes two 1-minute cuff inflations—one at 60 mmHg and one at 100 mmHg. In the illustrated example, the display for angiosome c (lateral plantar artery) remains normally perfused; the display for angiosome e (peroneal artery) shows some improvement (as indicated by the rounded peaks); and the display for angiosome a (posterior tibial artery) shows significant improvement, indicating that the stent was successful.

The apparatus described above in connection with FIGS. 1-4 may also be used to perform a second method of monitoring treatment of peripheral artery disease. This method comprises (a) using diffuse optical imaging to determine a first level of perfusion in each of a plurality of angiosomes of the limb; (b) performing a first surgical intervention to increase perfusion in a first one of the plurality of angiosomes; (c) using diffuse optical imaging to determine a second level of perfusion in each of the plurality of angiosomes after the first surgical intervention; (d) determining if at least one of the second levels of perfusion is indicative of PAD; (e) if a determination is made that at least one of the second levels of perfusion is indicative of PAD, performing a second surgical intervention to increase perfusion in a second one of the plurality of angiosomes; (f) using diffuse optical imaging determine a third level of perfusion in each of the plurality of angiosomes after the second surgical intervention; and (g) determining if the third level of perfusion in the second one of the plurality of angiosomes is still indicative of PAD. At least steps (b)-(g) are performed during a single surgical session (e.g., a session that begins when the patient is anesthetized and ends when the patient wakes up). A single surgical session will typically be less than six hours, and will always be less than 24 hours.

In some embodiments of the second method, steps (a)-(g) are all performed during the same surgical session.

Some embodiments of the second method further comprise (h) if a determination is made that the third level of perfusion in the second one of the plurality of angiosomes is still indicative of PAD, performing a third surgical intervention to increase perfusion in the second one of the plurality of angiosomes. At least steps (b)-(h) are performed during the same surgical session.

In some embodiments of the second method, the plurality of angiosomes includes an angiosome corresponding to a posterior tibial artery and an angiosome corresponding to a lateral plantar artery. In some of these embodiments, the plurality of angiosomes further includes an angiosome corresponding to at least one of an anterior tibial artery and a dorsalis pedis artery. In some of these embodiments, the plurality of angiosomes further includes an angiosome corresponding to a medial plantar artery.

SECTION 2: A Non-Contact Fiber-Less Diffuse Optical Tomographic System for Dynamic Imaging of the Feet with Peripheral Artery Disease.

Peripheral arterial disease (PAD) is primarily caused by atherosclerosis in the arteries that supply blood to the legs.

Dynamic vascular optical tomographic imaging (DVOTI) may be used for diagnosing and monitoring PAD. In some embodiments, the patient places his or her foot above a window in a monitoring device, and no contact is required to the upper portion of the patient's foot. This can be extremely advantageous in situations where the upper surface of the patient's foot is compromise e.g. with sores and/or ulcers). A spot of illumination light (preferably laser illumination) is directed onto different positions on the top of the patient's foot to illuminate the tissue from various projections. A first portion of that illumination light is diffusely reflected from the top of the foot. That diffusely reflected light is captured and processed to extract information about the blood flow near the top surface of in the patient's foot. A second portion of the illumination light passes through the patient's foot and through the window beneath the patient's foot. This second portion of light is also captured and processed to extract information about the blood flow through the patient's foot. Multiple views of feet are captured for dynamic tomographic imaging of foot vasculature using both reflectance and transmission-based geometries.

In the FIG. 7C-7G embodiments, a seated patient places his or her foot inside the imager on an angled foot platform. This posture is comfortable for the patient and provides the best and most consistent physiological signal. Light from two laser diodes are time-series multiplexed by an optical MEMS switch, collimated to a 2D galvanometer, and sequentially delivered to different positions on the top of the foot. The 2-D galvanometer can position the illumination light to the desired positions on top of the foot.

In some embodiments, the light is non-ionizing deep red and near-infrared light (e.g., between 650 nm and 900 nm), and the light is used to probe functional changes in biological tissues due to the characteristic absorption spectra of deoxyhemoglobin (Hb) and oxyhemoglobin ($HbO_2$) in blood that is present in the foot. In some embodiments, laser diodes are used for illumination (e.g., using a pair of laser diodes at 660 and 860 nm).

In the FIG. 7C-7G embodiment, illumination light arrives at various positions along the top of the foot at sequential times, based on the position of the 2-D galvanometer which is controlled by a controller. The top portion of the foot lies within the field of view of a camera-based detector such that diffusely reflected light can be recorded. A portion of the illumination light is diffusely reflected. This diffusely reflected light is attenuated by a filter and captured by an EMCCD camera. Another portion of the illumination light is transmitted through the foot. The foot platform contains a window at the mid-metatarsal level of the foot to allow transmitted light to pass. After passing through the foot, this light is reflected by a system of mirrors back to the same camera that is used to capture the diffuse reflected light. Each portion of captured light is used to obtain tomographic images. This configuration allows a single scanner positioned above and a single camera positioned above the foot to measure both reflected light and light that has been transmitted through the foot.

A light absorbing divider separates the diffusely reflected light from the transmitted light so that the camera image is divided into two regions. This is advantageous because the portion of light that has passed through the foot is much dimmer than the portion of light that is reflected off the top of the foot, so it is advantageous prevent the brighter reflected light from leaking into or polluting the smaller transmission signal that has passed through the foot. Optionally, in some embodiments, neutral density filters are inserted between the camera and the top of the foot reduce the source illumination spot and the reflected light intensity so that the dynamic range of the sensor is used efficiently.

In alternative embodiments, separate cameras can be used for the reflected light and the light that was transmitted through the foot.

The amount of transmitted light through the foot is low in comparison to diffusely reflected light and is limited by the power of the source illumination, the properties of the foot itself, and the placement of the foot, mirrors, and camera relative to each other. To maximize the amount of transmitted light reaching the camera and obtain the optimal positioning of the camera and mirrors, various combinations of camera heights and fields of view, number of mirrors, and mirror positions and angles were considered.

The combinations were modeled using Monte Carlo ray tracing simulations in TracePro (Lambda Research Corporation, Littleton, MA). To reduce computation time in the simulation, photons were emitted from the detector (Uniform angular distribution, 1 $W/m^2$) and the number of photons reaching the bottom of the foot was counted for each design. Additionally, the average optical path length difference between the diffusely reflected light and the transmitted light was also calculated and minimized to account for the limited focal depth of the camera. Varying the design parameters lead to trade-offs between the transmitted signal and the optical path length difference.

Figures 7A, 7B:
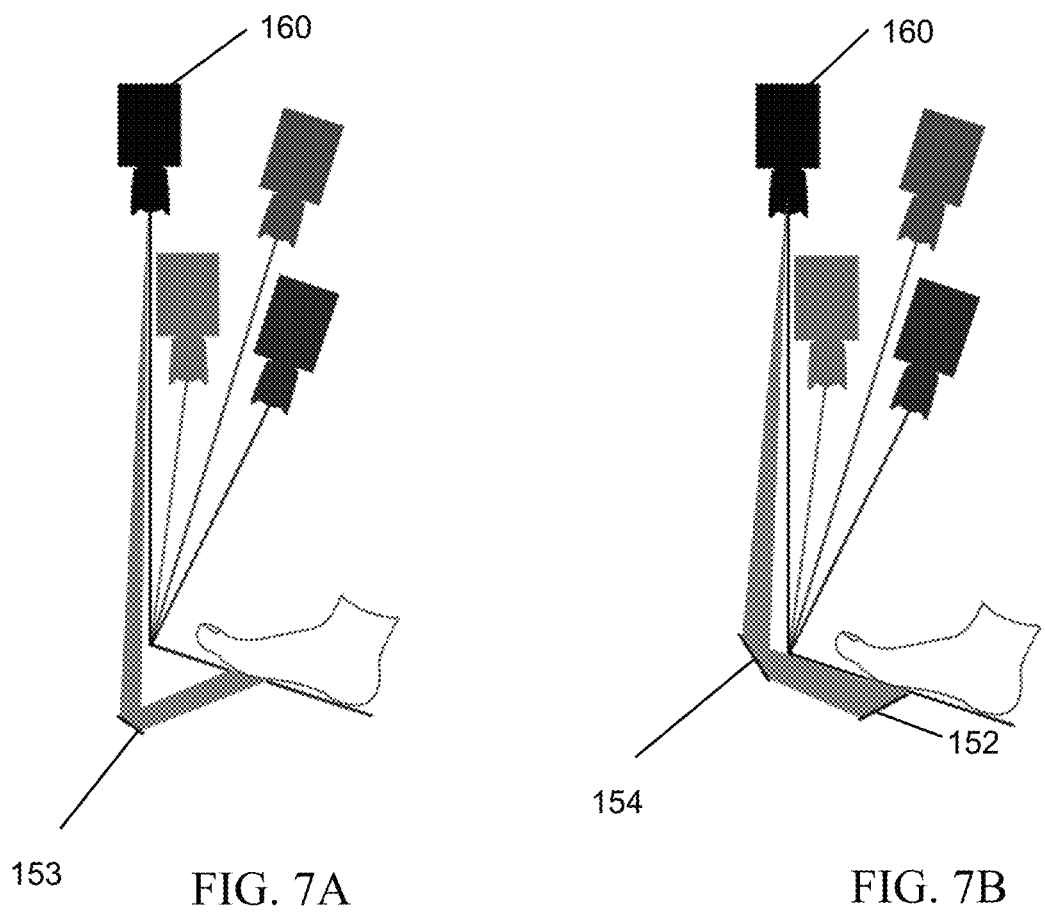
FIG. 7A depicts one configuration of a noncontact tomography system that was modeled.
FIG. 7B depicts another configuration of a noncontact tomography system that was modeled.

FIG. 7A depicts one configuration that was modeled. This configuration used a single mirror 153 positioned below the foot to direct the transmitted light back up to the camera 160. The position of the camera 160 was varied between different choices (four of which are shown in FIG. 7A), and the position of the mirror 153 was also varied it to arrive at the best configuration. FIG. 7B depicts another configuration that was modeled. This configuration used two mirrors 152, 154 positioned below the foot to direct the transmitted light back up to the camera 160. The position of the camera 160 was varied between different choices, and the position of both mirrors 152, 154 was also varied it to arrive at the best configuration. The FIG. 7B configuration provided better results than the FIG. 7A configuration, so the design depicted in FIGS. 7C-7G was selected as one of the preferred embodiments.

Figure 7C:
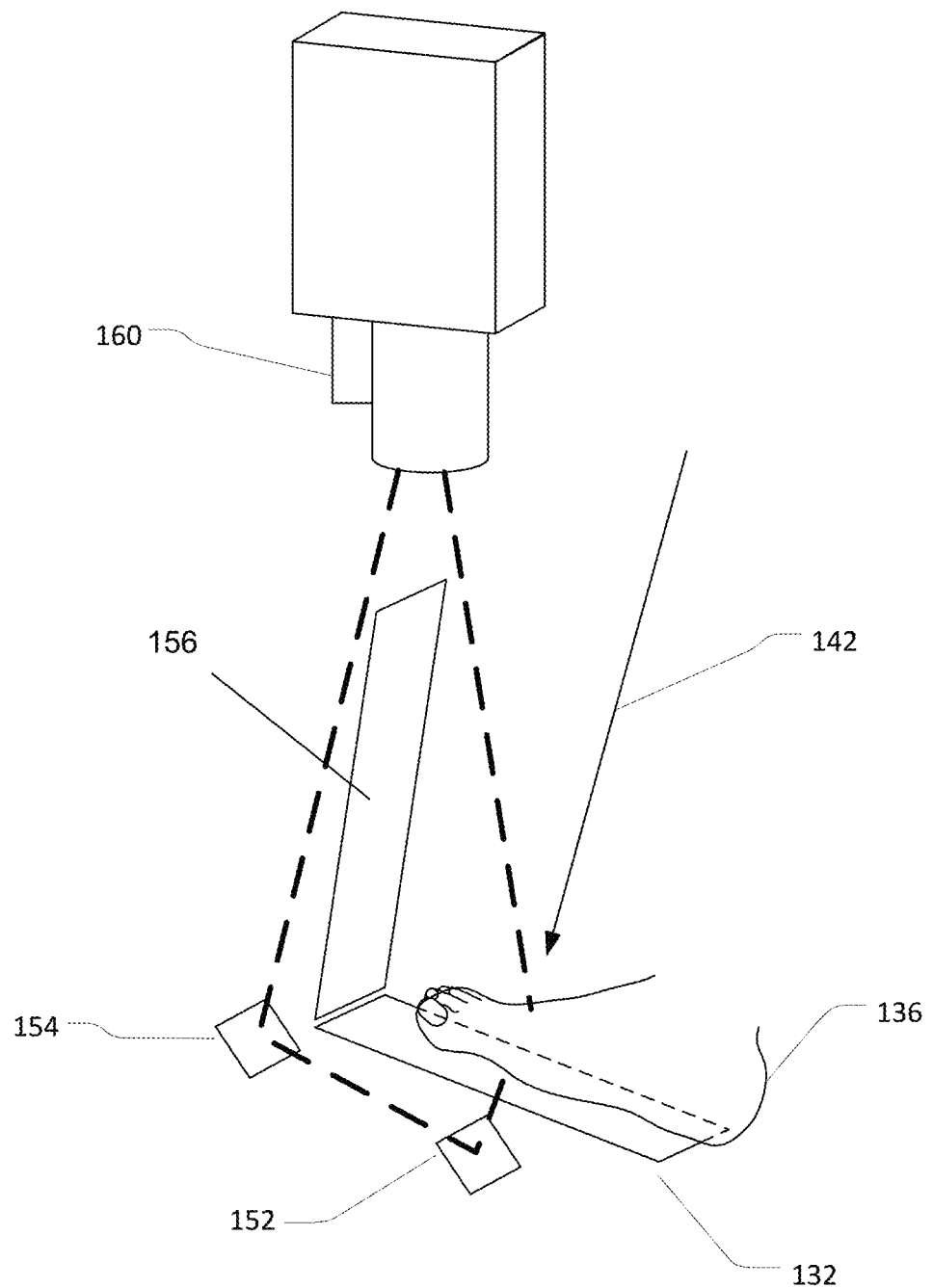
FIGS. 7C-7G depict various views of a console embodiment for performing noncontact tomography on a subject's foot.

The FIG. 7C configuration exhibits a good combination of maximizing the amount of light captured from the bottom of the foot through the mirror system (~16 dB SNR) and limiting the optical path length difference (~8 inches). This was a two-mirror design in which the first mirror facing the bottom of the foot captures the bottom of the foot while the second mirrors projects the images from the first mirror onto the camera. This overall design also allows an integrated source illumination and 3D geometry scanning without obstructing the camera's field of view. In an integrated system, the camera could also serve as the camera in a 3D scanner.

In the FIG. 7C-7G embodiment, the user's foot 136 is inserted into a chamber 130 (shown in FIG. 7G) and rested on a platform 132. A light source illuminates the top of the foot 136 with an illumination beam 142. A portion of that light is diffusely reflected back up to the camera 160. Another portion of that light is transmitted through the foot 136 and also passes through a window 150 in the platform 132. This light is then reflected by the two mirrors 152, 154 up to the camera 160. Tomographic images are obtained from both portions. One suitable way to prevent the light that has been reflected from the top of the foot from polluting the return of the light that has been transmitted through the foot is to use a light-tight divider 156 that separates the two light paths in FIG. 7C, which is cross-section view of optimized non-contact DDOT system design with reflectance and transmission-based geometry. In some embodiments, the surfaces of the divider 156 absorb light at the relevant wavelengths.

Figure 7D:
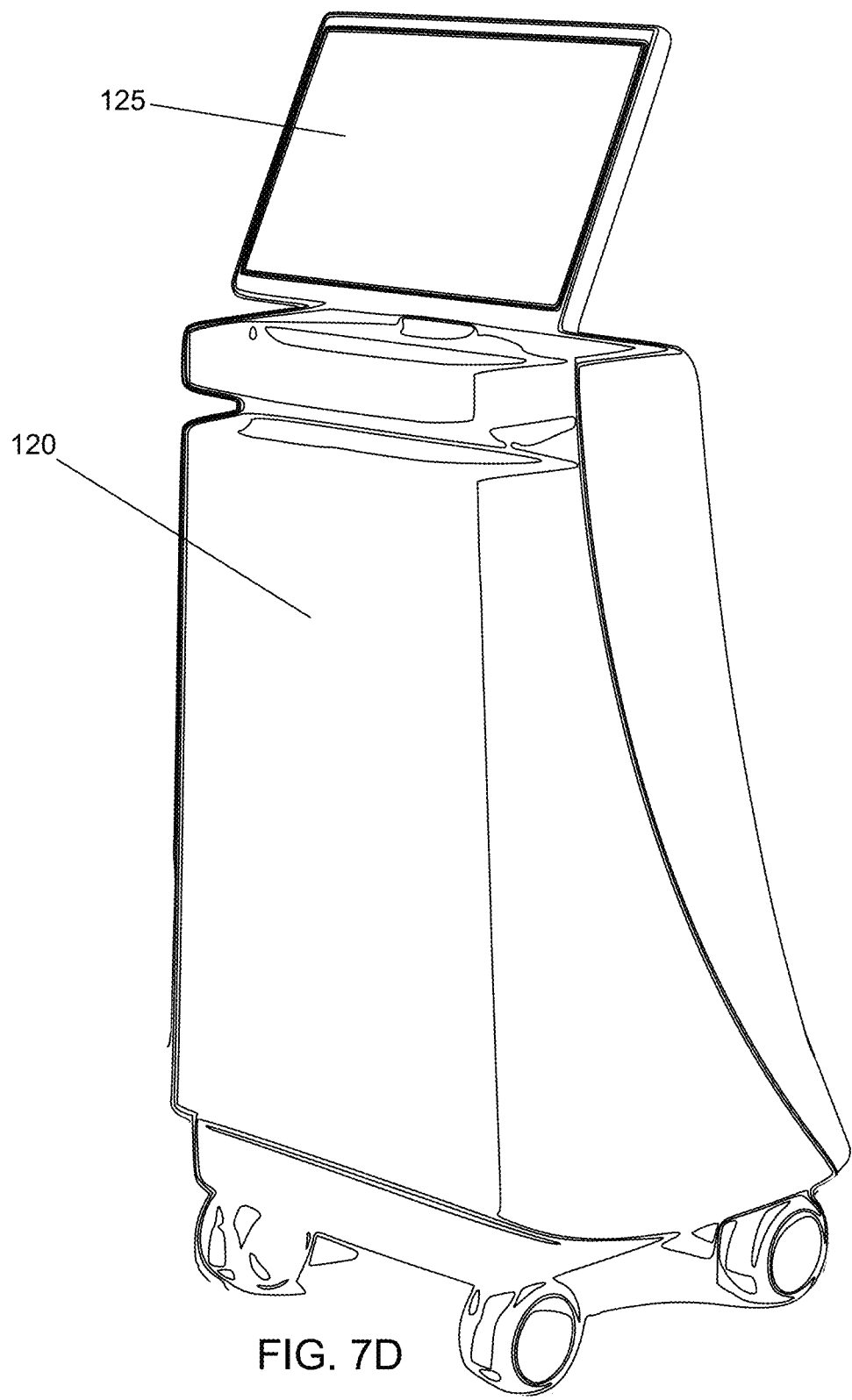
Figure 7E:
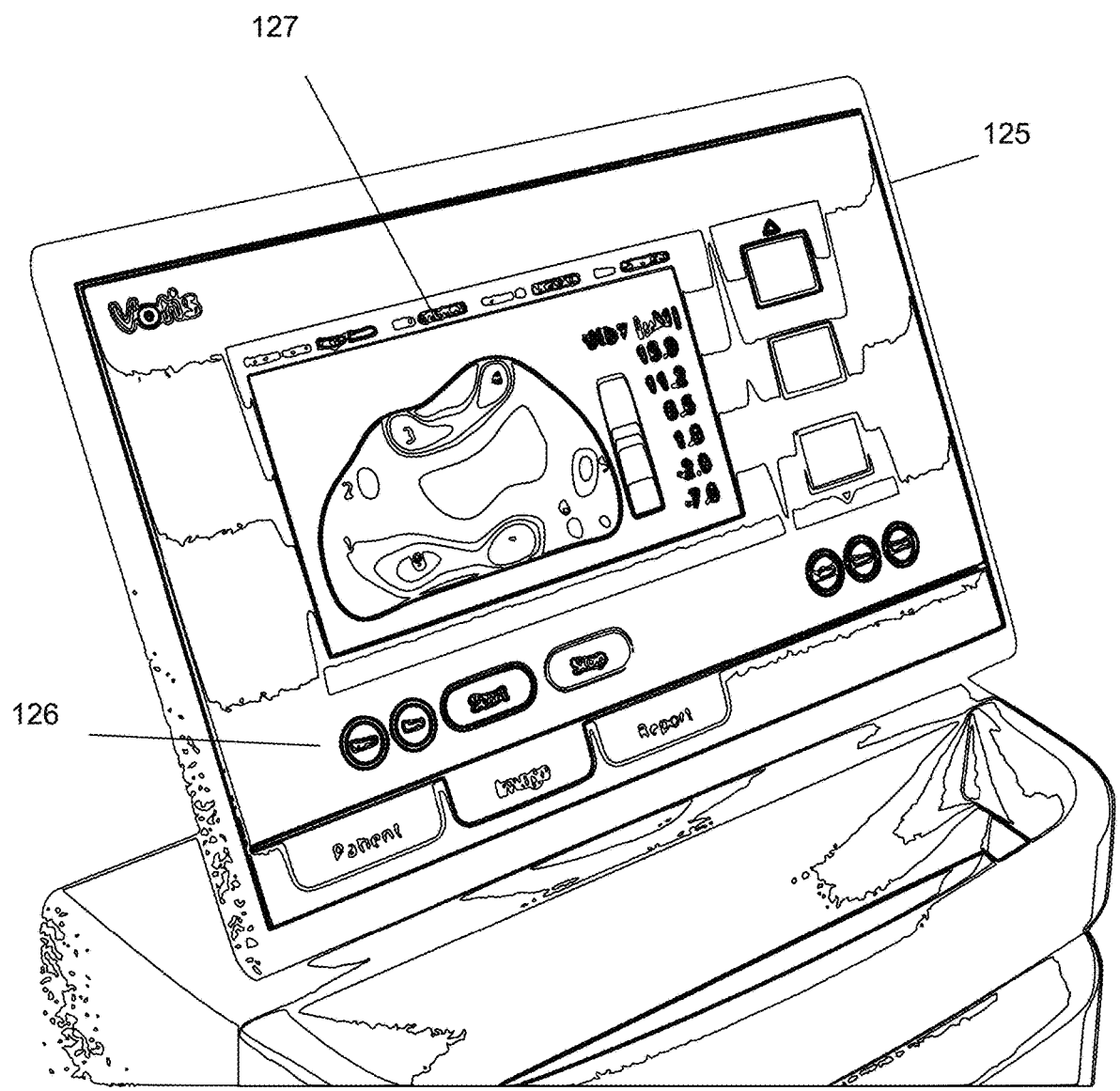
Figure 7F:
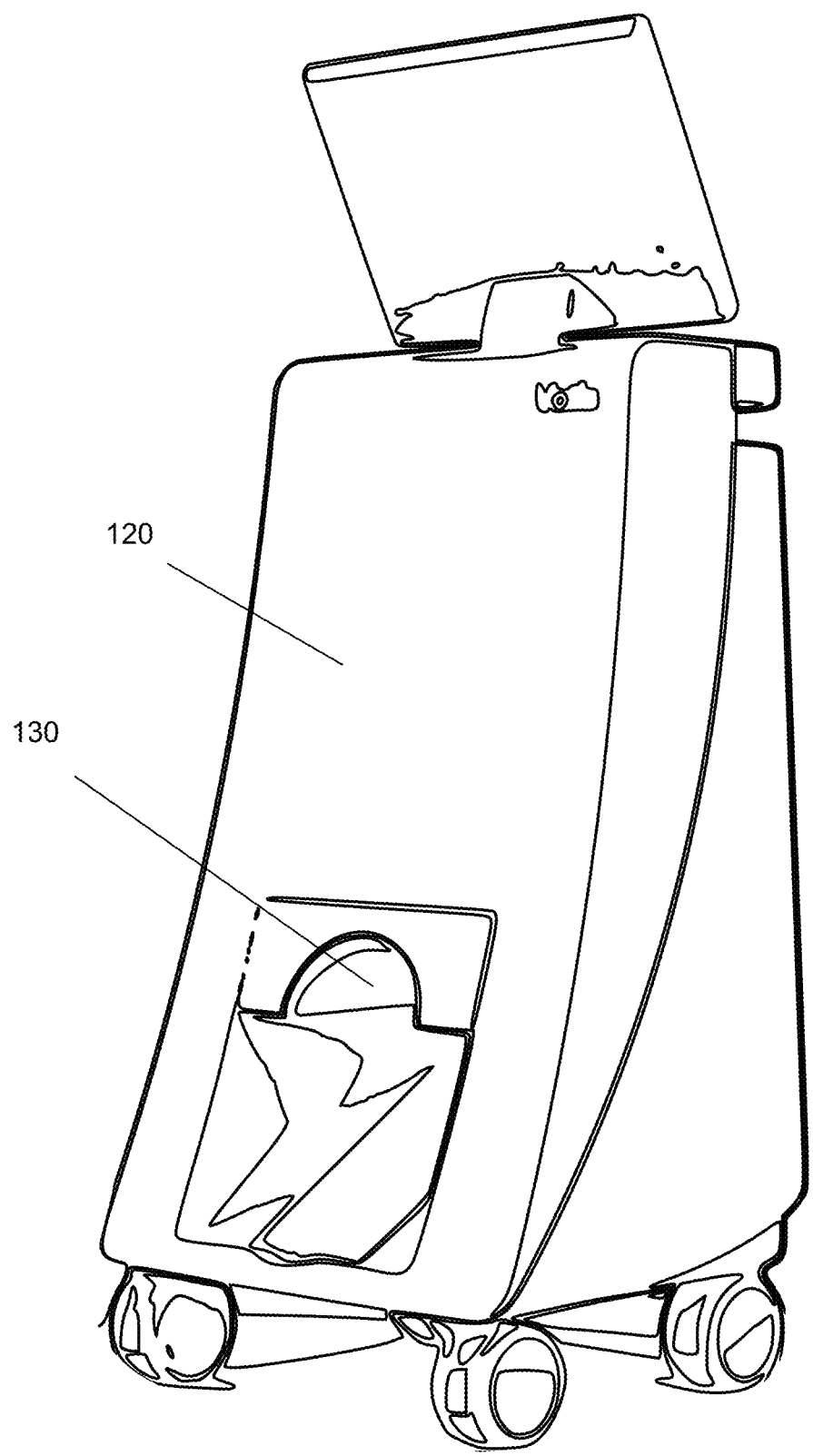

The optical design depicted in FIG. 7C may optionally be integrated into a console 120 with a user interface 125 as seen in FIG. 7D. The console 120 houses the optical components and associated processors for processing the detected light. The user interface 125 is used by the operator to operate the device. FIG. 7E depicts one example of a suitable user interface in the form of a touch screen. The touchscreen may include controls 126 and data displays 127. A wide variety of alternative user interfaces may be substituted for the user interface depicted in FIG. 7E, as will be apparent to persons skilled in the relevant art. FIG. 7F depicts the back side of the console 120. This view reveals the opening to the chamber 130 into which the foot of the patient is inserted in order to obtain measurements.

Figure 7G:
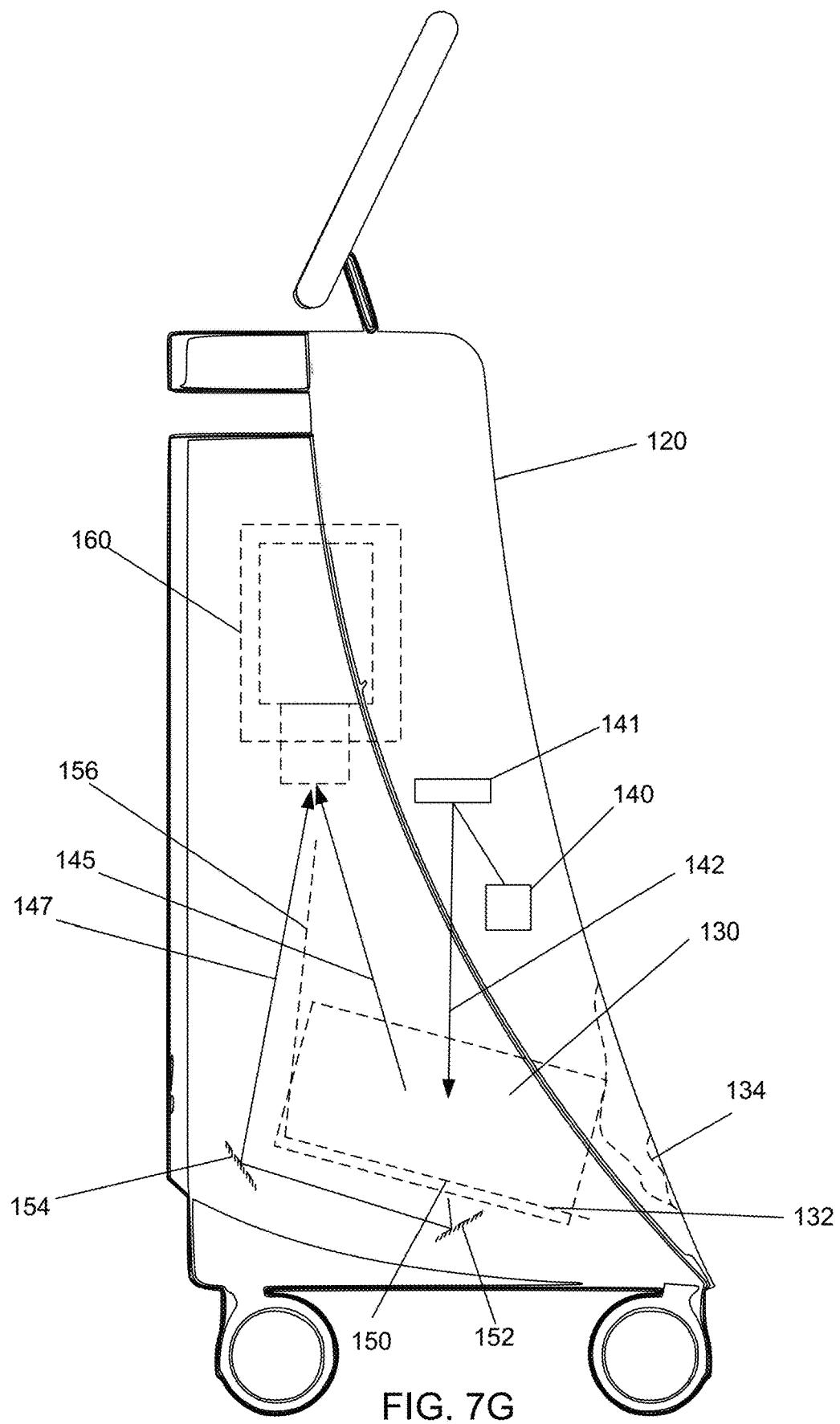

FIG. 7G depicts the layout of the optical components within the console 120. The patient inserts their foot into the chamber 130, and an optional light blocking boot or blanket 134 is positioned near the opening to the chamber 130 to prevent stray light from affecting the measurements. The light source 140, which in some embodiments comprises a pair of laser diodes at different frequencies, generates the illumination light. The illumination light is steered to a desired position on top of the patient's foot by an optical steering element 141. Examples of suitable steering elements 141 include 2D galvanometers and polygon mirrors mounted on a spindle. Source light 142 illuminates the top of the foot, and a portion of that light 145 is diffusely reflected back up to the camera 160. Another portion of that light 147 is transmitted through the foot and through the window 150 disposed in the foot-rest platform 132, and then reflected by the two mirrors 152, 154 up to the camera 160. A light-tight divider 156 that separates the two light paths.

To qualitatively characterize the system's ability to detect spatial changes, images of a solid phantom with cylindrical absorbers at various depths were captured.

Figure 8A:
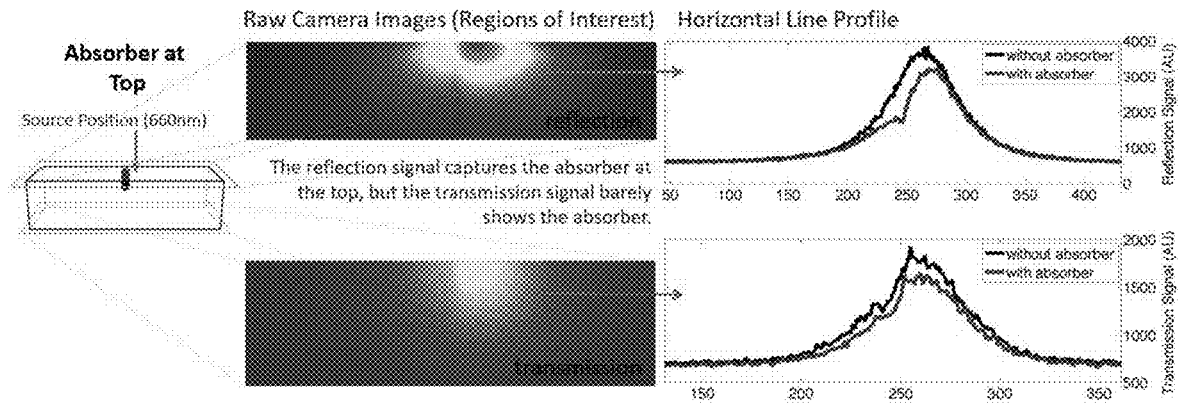
FIGS. 8A-8C shows raw camera images that simultaneously captured the top and bottom of a solid phantom.
Figure 8B:
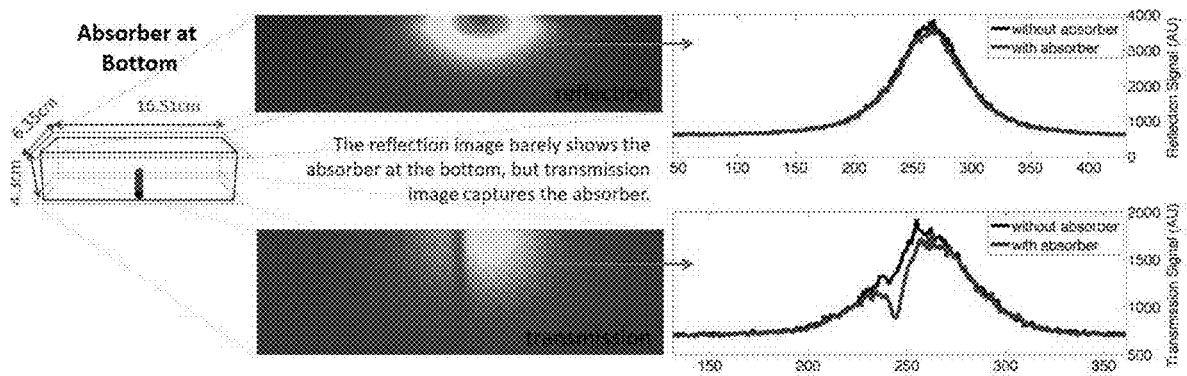
Figure 8C:
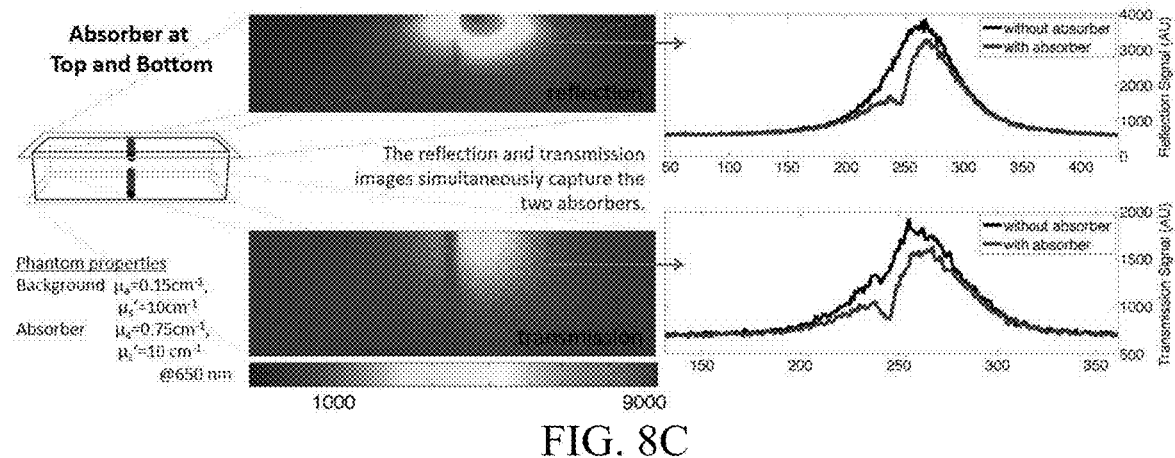

FIGS. 8A-8C shows raw camera images that simultaneously captured the top and bottom of a solid phantom (i.e., the reflection and transmission regions, respectively) with the absorber at the top (FIG. 8A), bottom (FIG. 8B), and top and bottom (FIG. 8C) of the block phantom. The transmission portion of the images are very similar to the data from conventional contact-based transmission-based system and indicate that the detection of absorbers at different depths is improved with multiple viewing angles. The line profiles on the right side of the panels show that the presence of an absorber at the top is not as apparent in the transmission signal, but is readily seen in the reflection signal Optionally, an occlusion cuff may be used in conjunction with any of the embodiments described above, in which case one set of tomographic images may be obtained when the occlusion cuff is not activated and a second set of tomographic images may be obtained when the occlusion cuff is activated.

SECTION 3A: Modeling of the Hemodynamics in the Feet of Patients with Peripheral Artery Disease.

The models and algorithms described below in this appendix may be used in conjunction with the embodiments described above. They may be used in connection with systems in which a portion of illumination light that arrives at the top of the foot is diffusely reflected and monitored, and another portion of the illumination light is transmitted through the foot). The models and algorithms described below may also be used in systems with non-contact illumination that measure diffusively reflected light alone, or in systems with non-contact illumination that rely on transmission through the foot alone. The models described below may also be used in systems in which the illumination source does make contact with the foot (e.g., the embodiment described above in connection with FIGS. 1-4 or systems that use fiber optics to route light from the sources to the foot and from the foot back to the detectors).

Vascular Optical Tomographic Imaging (VOTI) that allows to monitor the hemodynamic effects in the foot of PAD patients as a result of a venous occlusion in the upper or lower thigh. This application describes a novel mathematical model that allows us to simulate hemodynamic effects in feet caused by thigh cuff occlusion. The model, written in MATLAB, is based on a multi-compartmental Windkessel model where dynamic effects related to the occlusion of the veins and, to a lesser extent, of the arteries are considered. The circulatory system for the leg is represented using electrical equivalents (e.g., resistors, capacitors, and inductors) to model the blood flow and pressure drop. The model was validated by fitting simulated data with experimental data acquired from both healthy subjects and PAD patients. The fittings obtained were of good quality and their analysis allowed us to improve the accuracy, specificity, and sensitivity beyond those of previous methods, to the 90-95% range.

These models are used with vascular optical tomographic imaging system (VOTIS). The system employs optical techniques to measure the transmitted and reflected light to estimate hemoglobin distribution and tissue scattering coefficients inside the foot.

To explain the hemodynamic behavior, we have developed a computational model of the vascular system under consideration.

The model we propose in this application goes beyond previously considered approaches in several ways. Our objective was not to estimate the shape of the blood pulse, or compare two different system states, but to model the time-dependent dynamic accumulation of the blood in the foot due to a cuff occlusion of the veins in the leg. Hence, we developed a modular model based on an analogy to electrical components to allow for hemodynamic effects. In particular, we introduced a dynamic variable resistor to represent the cuff inflation/deflation and evaluated the changes in pressures in the various compartments during the cuff inflation/deflation. Employing the newly-created model and comparing the results obtained with the experimental clinical data previously acquired, we gained further insights into the physiological underpinnings of the observed effects. As we will show, this in turn led to improved diagnostic sensitivity and specificity.

SECTION 3B: Methods

Acquisition of Experimental Data

In a previous study, 20 healthy volunteers and 20 PAD patients were recruited at the Division of Vascular Surgery at New York Presbyterian Hospital—Columbia University. Ten of the 20 PAD patients were diabetic. The diagnosis was performed by the two collaborating physicians based on a combination of the patients' ABI readings, segmental ultrasound waveforms, physical symptoms, and medical history.

Datasets from one healthy patient were corrupted during post processing and were not available for the model analysis. The remaining data used for the analysis in this application included VOTIS measurements from 19 healthy volunteers and 20 PAD patients of which 10 also had diabetes.

The VOTI system used during the experiments employed a total of 34 optical fibers, of which 14 were connected to light sources and 20 were connected to Si photodetectors.

The fibers formed a coronal cross section at the mid-metatarsal level of the foot. This region was chosen to evaluate the vessels that supply the forefoot, the most common location for diabetic foot ulcers. Our VOTI systems operated at two wavelengths (λ1=760 nm and λ2=830 nm) and full tomographic data sets were obtained with a frame rate of approximately 6 Hz.

A dynamic imaging protocol of five 1-minute phases was used to collect the data from the patients. The patients were in a sitting position with their foot placed inside the measuring system and a pressure cuff wrapped around their upper thigh. The measurements started with a resting phase in which a baseline signal was recorded; in the second phase the cuff was inflated to 60 mmHg; in the third phase the cuff was rapidly deflated and the signal was allowed to return to the baseline; in the fourth phase a second cuff inflation was performed, this time with 120 mmHg; finally, the cuff was deflated and the signal recorded for another minute.

The aim during the cuff inflations was to obtain a venous occlusion. In this case the blood keeps being supplied to the foot through the arteries but its return to the heart is impeded. This results in pooling of the blood in the foot, which in turn leads to increased light absorption. Two different pressures were used for the thigh cuff to evaluate which level leads to a better distinction between PAD patients and healthy volunteers.

The resulting data was input to a diffusion-theory-based PDE-constrained multispectral image reconstruction algorithm. For each patient two series of 1000 cross-sectional images were generated with a frame rate of about 2.75 frames per second; one series showing spatio-temporal changes of deoxy-hemoglobin ($\Delta[Hb]\%$) as compared to baseline; and one series showing spatio-temporal changes of oxy-hemoglobin ($\Delta[HbO_2]\%$) as compared to baseline.

Figure 9:
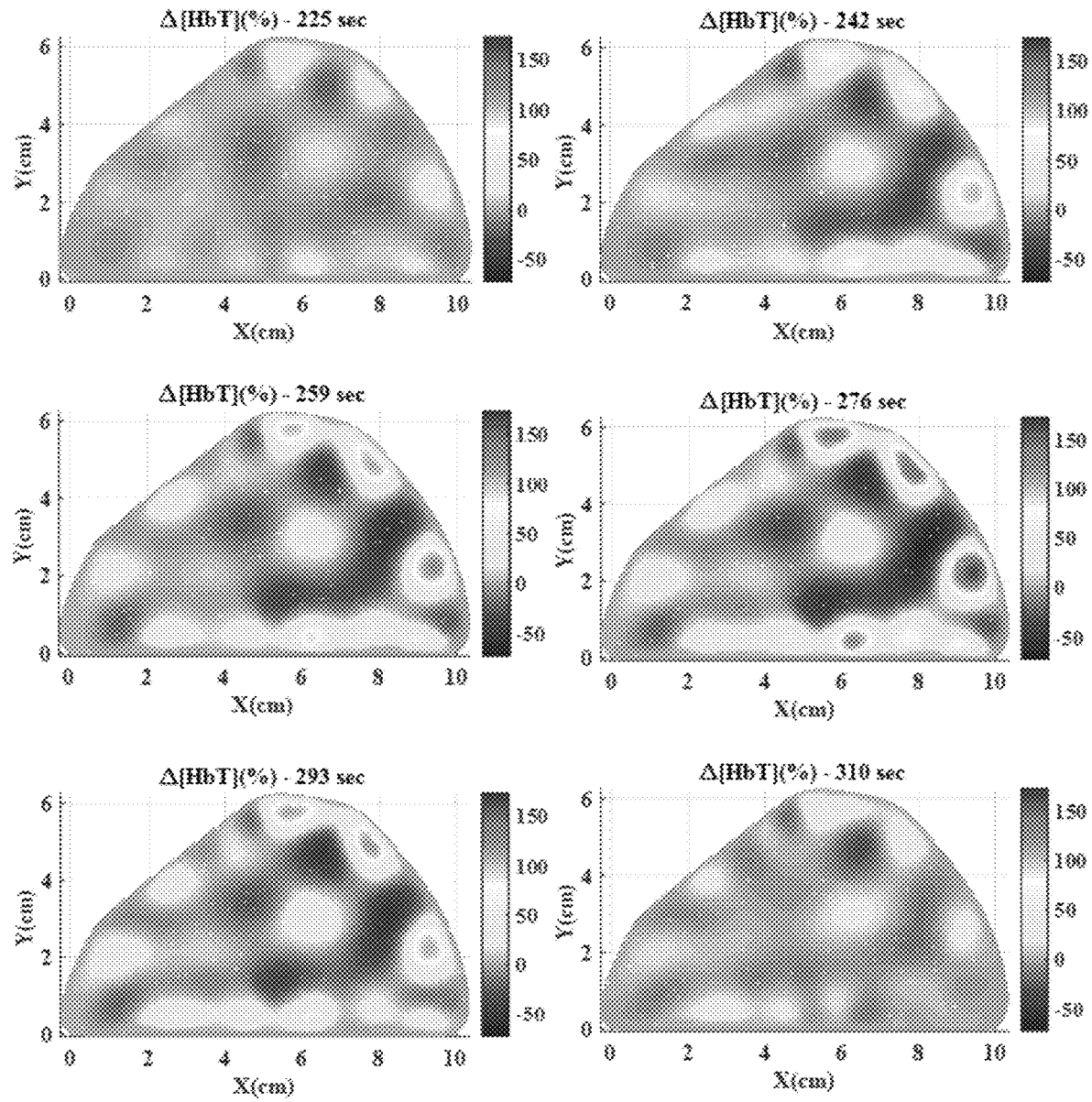
FIG. 9 shows selected images of a series for a healthy patient.

As an example, FIG. 9 shows selected images of such a series for a healthy patient. More specifically, shown are 6 out of 1000 cross-sectional images obtained during an experimental measurement. Displayed are the % changes in total hemoglobin concentration ($\Delta[HbT]\%$) at various moments before, during and after the cuff inflation and deflation. The changes are largest at 276 seconds, just before the release of the cuff.

Figure 10:
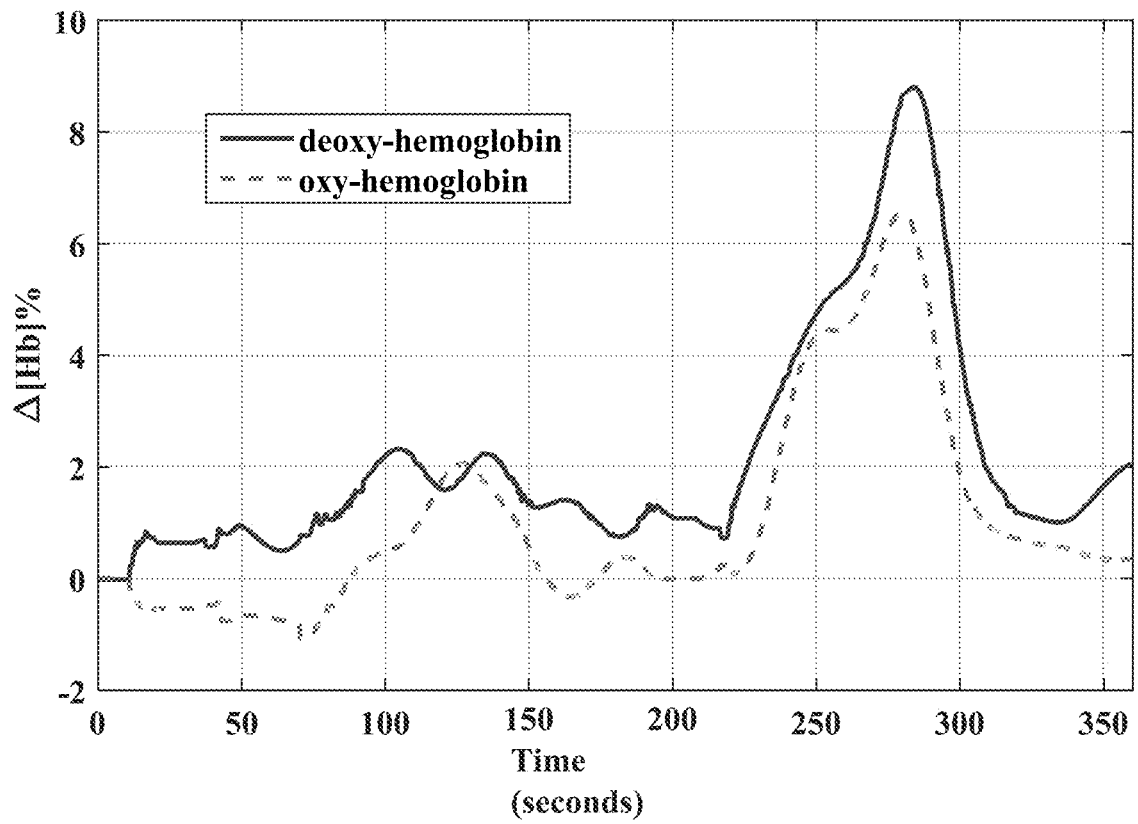
FIG. 10 shows the temporal map of the deoxy- and oxy-hemoglobin distributions in a group of foot cross sections.

FIG. 10 shows the temporal map of the deoxy- and oxy-hemoglobin distributions in all the foot cross section are shown and the percentage change of deoxy—(solid curve) and oxy—(dotted curve) hemoglobin distributions in the foot cross section.

To compare the changes observed during the cuff experiment in PAD patients with changes observed in healthy volunteers, one has to define regions of interest for each subject. In each subject locations of major changes are different, as foot sizes and vascular anatomy vary from subject to subject. To this end we calculated for each individual subject the cross-correlation coefficients between the area weighted average change in total hemoglobin over the whole cross section and the change in total hemoglobin for each pixel within the cross section over time were considered:

$$\rho = \frac{\sum_{t=0}^{N-1}(h(t)-\mu_h)\cdot(W(t)-\mu_W)}{\sum_{t=0}^{N-1}\sqrt{(h(t)-\mu_h)^2}\cdot\sum_{t=0}^{N-1}\sqrt{(W(t)-\mu_W)^2}}. \quad (6)$$

Figure 11:
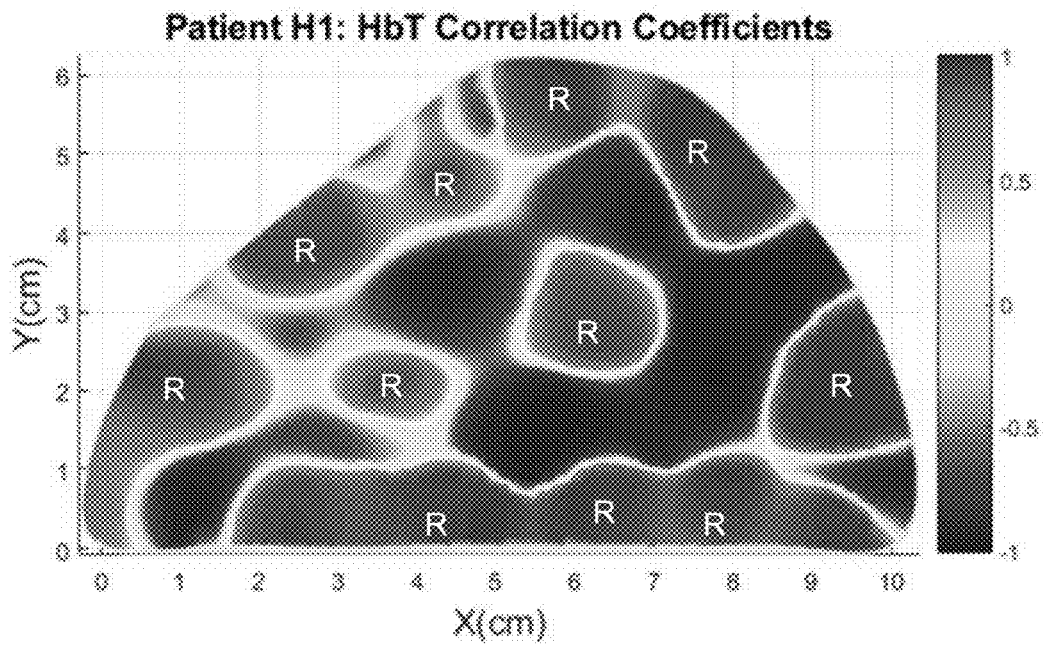
FIG. 11 shows a typical estimated cross-correlation map of coefficients in the cross sectional image of the foot for one PAD patient.

Here h(t) is an individual pixel time trace from within the foot, W(t) is the weighted average signal from the entire foot and $\mu_h$ and $\mu_w$ are their respective mean values in time. A typical estimated cross-correlation map of coefficients in the cross sectional image of the foot for one PAD patient is shown in FIG. 11. Note that one can clearly identify regions in which the local hemodynamic effects correlated strongly with the overall global hemodynamic effects. The regions marked "R" (in which the correlation coefficient is high) correspond to the locations of the main vasculature in the foot.

In our previous study, we found that a value of $\rho_c$=0.7 leads to most significant differences between patients affected by PAD and healthy volunteers, which in turn resulted in highest diagnostic sensitivities and specificities. Therefore, we used the same value here for evaluating and fitting our model.

Figure 12:
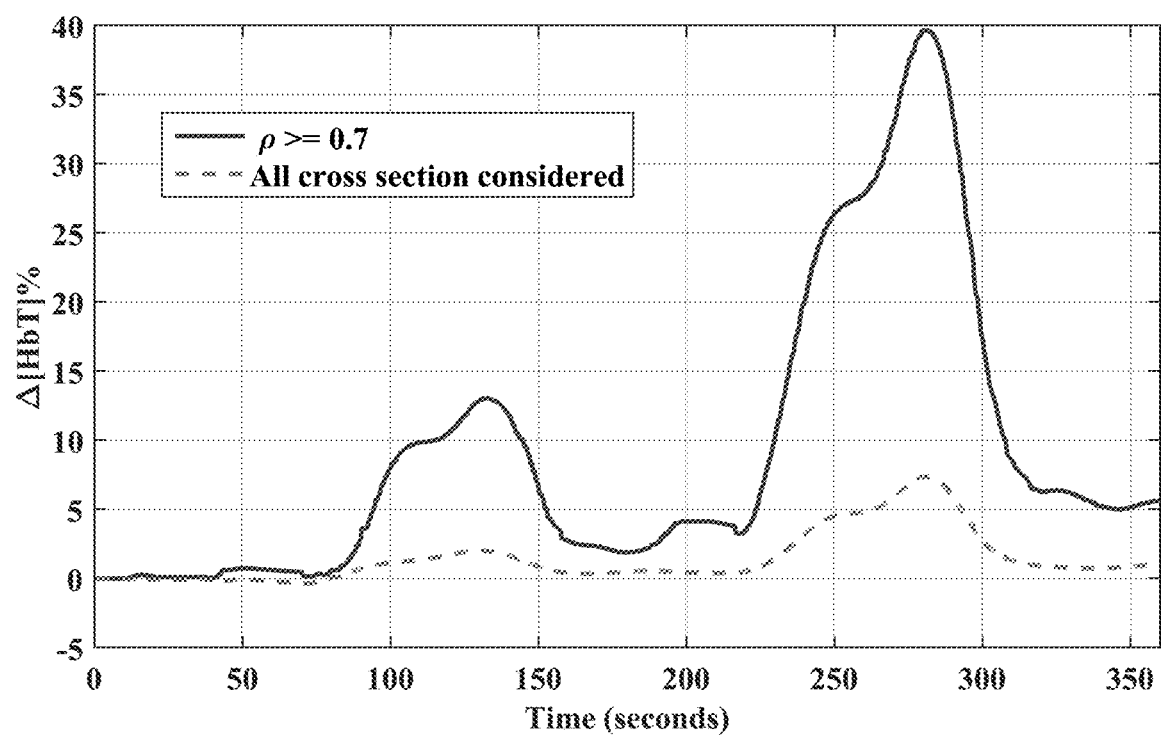
FIG. 12 shows a comparison between the mean total hemoglobin variation in all foot cross section and in a selected region.

Averaging the total hemoglobin variation over all pixels in the image with $\rho=\geq\rho_c$ and doing this for all time steps $\Delta t$, we obtain a similar curve to FIG. 10. However, now this curve shows the changes not in all the foot cross section, but only in all regions with $\rho=\geq\rho_c$. A comparison between the mean total hemoglobin variation in all foot cross section and just in the selected region is shown in FIG. 12, which is the temporal map showing the percentage change of total hemoglobin distribution considering all the cross-sectional area (dotted curve) and only the regions in which $\rho>\sim0.7$ (solid curve).

Development of the Improved Model.

To assess the dynamic accumulation of blood in the foot of healthy and PAD patients, we adopted a multi-compartmental derivation of the Windkessel model. In our model, each subsection of the vasculature is represented by a combination of capacitors (representing the vessels' elasticity and compliance), resistors (representing the resistance to the blood flow), and inductors (representing the blood inertia). The blood pressure and flow were modeled with a voltage and a current respectively. To represent the relationship between the drop in pressure in each vascular compartment and the blood flow through it, using the electrical analogy, was used Ohm's Law (V=R·I) and a set of first-order differential equations to represent the capacitors $$\left(C\cdot\frac{dV}{dt}=I\right)$$

and inductors $$\left(L\cdot\frac{dI}{dt}=V\right).$$

Figure 13:
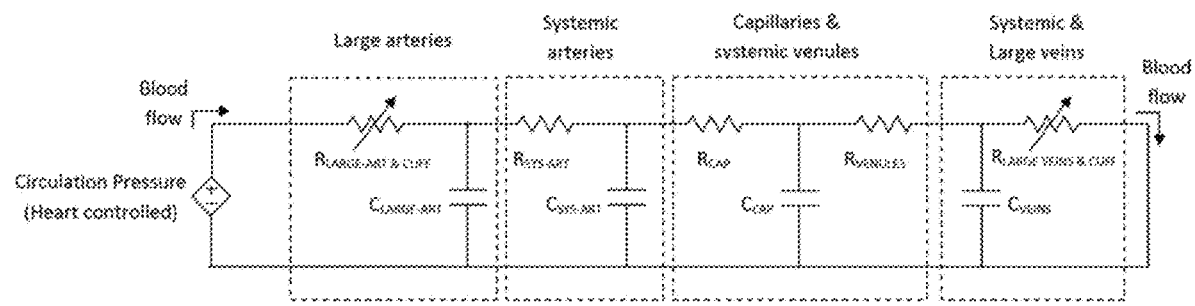
FIG. 13 is an equivalent electrical schematic diagram of a model that was implemented.

Our initial studies with this model suggested that the effects of the inductors, which are used to portray fast changes in the blood flow, were negligible compared to the effects of the other components. This is not surprising, since we are interested in the accumulation of blood in the foot over a minute-long cuff inflation, and hence fast changes (on a sub-second or second-scale) in the blood flow do only play a minor role. Consequently, we simplified the model and reduce the total number of parameters present in the system. As a result, the final model we implemented consisted of four sub-sections: (1) large arteries; (2) systemic arteries; (3) capillary bed and systemic venules; and, (4) large veins. Each resistor was connected in series to the following resistor, whereas the capacitor was connected in parallel to the following compartments, forming a ladder circuit, as seen in FIG. 13, which is equivalent electrical schematic diagram of the model that was implemented.

During our clinical VOTIS measurement protocol, we used a thigh cuff to occlude the veins that carry the blood back to the heart. In particular, during a single experimental acquisition, two consecutive 1-minute cuff inflations were applied, separated by a 1-minute interval between them. The first and second cuff were inflated to 60 and 120 mbar, respectively. To simulate the inflation and deflation of these cuffs, the resistances used for the main veins and arteries sections were considered variable and increasing during an inflation. The cuff inflation causes a reduction of the blood flow through the blood vessel at the cuff location and a correspondent increment in the pressure before that location. After the deflation, this pressure decreases again to the resting value.

The cuff was operated manually, and hence maximum pressures of 60 and 120 mbar were not obtained immediately. To model this effect, we explored linear and exponential functions in simulations of the increasing/decreasing values for the resistances. We found that exponential fits provided a better match with the data than linear fits.

Furthermore, veins are closed before arteries become compressed in cuff experiments. Hence, we employed a delay parameter that is accounting for this fact in our simulations. The following system of four first-order differential equations was thus generated:

$$\begin{cases} \frac{dV_{CL}}{dt} = -\left(\frac{1}{C_{LA}R_{LA}(t)} + \frac{1}{C_{LA}R_{SA}}\right) \cdot V_{CL} + \frac{1}{C_{LA}R_{SA}} \cdot V_{CS} + \frac{V_{Heart}(t)}{C_{LA}R_{LA}(t)} \\ \frac{dV_{CS}}{dt} = \frac{1}{C_{SA}R_{SA}} \cdot V_{CL} - \left(\frac{1}{C_{SA}R_{SA}} + \frac{1}{C_{SA}R_C}\right) \cdot V_{CS} + \frac{1}{C_{SA}R_C} \cdot V_{CC} \\ \frac{dV_{CC}}{dt} = \frac{1}{C_C R_C} \cdot V_{CS} - \left(\frac{1}{C_C R_C} + \frac{1}{C_P R_{VEN}}\right) \cdot V_{CC} + \frac{1}{C_C R_V} \cdot V_{CV} \\ \frac{dV_{CV}}{dt} = \frac{1}{C_V R_V} \cdot V_{CC} - \left(\frac{1}{C_V R_V} + \frac{1}{C_V R_V(t)}\right) \cdot V_{CV} \end{cases} \quad (7)$$

Where:

$$R_V(t) = R_V + R_{CUFF-V}(t). \quad (8)$$

$$R_{CUFF-V}(t) = \begin{cases} 0 & t_{start} \to t_{start\_infl} \\ \exp func0 \to R_{CUFF-V} & t_{start\_infl} \to t_{end\_infl} \\ R_{CUFF-V} & t_{end\_infl} \to t_{start\_defl} \\ \exp funcR_{CUFF-V} \to 0 & t_{start\_defl} \to t_{end\_defl} \\ 0 & t_{end\_defl} \to t_{end} \end{cases} \quad (9)$$

$$R_{LA}(t) = R_{LA} + R_{CUFF-LA}(t). \quad (10)$$

$$R_{CUFF-LA}(t) = \begin{cases} 0 & t_{start} \to t_{start\_infl} + \Delta t \\ \exp func0 \to R_{CUFF-V} \cdot X & t_{start\_infl} + \Delta t \to t_{end\_infl} \\ R_{CUFF-V} \cdot X & t_{end\_infl} \to t_{start\_defl} \\ \exp funcR_{CUFF-V} \cdot X \to 0 & t_{start\_defl} \to t_{end\_defl} \\ 0 & t_{end\_defl} \to t_{end} \end{cases} \quad (11)$$

Where $t_{start}$ is the starting time of the data collection, $t_{start\_infl}$ is the starting time for the cuff inflation, $t_{end\_infl}$ is the ending time of the cuff inflation, $t_{start\_defl}$ is the starting time for the cuff deflation, $t_{end\_defl}$ is the ending time of the cuff deflation, $t_{end}$ is the ending time of the data collection, $\Delta t$ is a delay before the arteries are affected by the cuff, X is a multiplication factor between 0 and 1 that links the cuff effect on the veins and arteries.

The solutions of this system can be approximated using the Euler method considering a narrower time step than the one used to characterize the heartbeat. The model was implemented and solved in MATLAB. A graphic user interface was created to facilitate the manipulation of the different parameters. The heartbeat was modeled using typical electrocardiogram and physiological pressures: heart rate of 75 beats/min, systolic pressure of 120 mmHg and diastolic pressure of 80 mmHg. The cuff inflation and deflation times used were set to mean values obtained from experimental tests. Overall, the total number of variables changed in the simulations was 11. This includes the five resistances ($R_{LA}$ for the large arteries, $R_{SA}$ for the systemic arteries, $R_C$ for the capillaries, $R_{VEN}$ for the systemic venules, and $R_V$ the systemic and large veins), the four capacitances ($C_{LA}$ for the large arteries, $C_{SA}$ for the systemic arteries, $C_C$ for the capillaries and venules, and $C_V$ for the veins), and two resistance values ($R_{CUFF-V}(t)$ and $R_{CUFF-LA}(t)$) directly correlated between them, to show the effect of the cuff inflation respectively on the large arteries and veins.

SECTION 3C: Results

Figure 14:
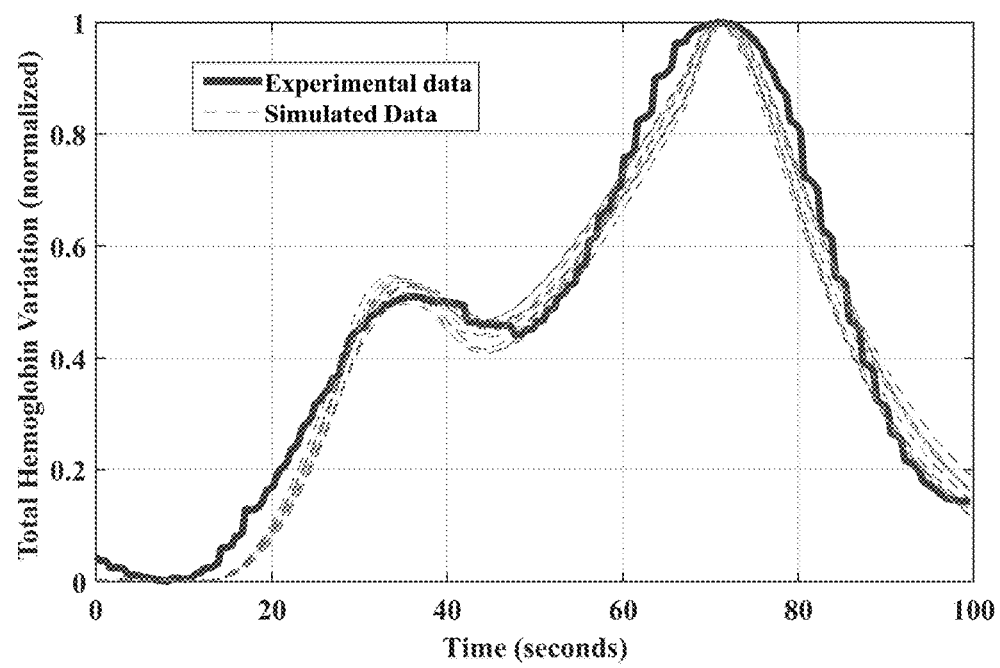
FIG. 14 depicts an example of a typical hemodynamic response during a cuff inflation and deflation.

An example of a typical hemodynamic response during a cuff inflation/deflation is shown in FIG. 14 (solid curve). Here the cuff is inflated at t=10 seconds. Subsequently we can see an increase in total hemoglobin for about 20 seconds, before a first plateau is reached. Sometimes, as in the case shown, this plateau becomes a "dip" in which ΔHbT]% briefly decreases, before a further increase is observed.

FIG. 14 shows an example of a typical hemodynamic response to a cuff inflation/deflation recorded with our VOTI system (solid curve) Also shown are 10 "best" fittings (dotted curves) obtained automatically by the program. Note that in FIG. 14, a second maximum is reached at t=70 second. At that point the cuff is deflated and ΔHbT]% returns to baseline.

To fit this curve and obtain a better understanding about the physiological underpinning, we started our analysis by varying all 11 model parameters over suitable physiological ranges.

The obtain starting values for the RC parameters We decided to firstly find possible ranges for each parameter in order to obtain expected quantities of flows and pressure drops between model sections.

With the ranges and step sizes given in Table I, we created about 20 million curves reflecting approximately 20 million possible combinations of the 11 variables.

TABLE I

VARIABLES RANGE

| Variable Name | Min Value | Step | Max Value |
|---|---|---|---|
| $R_{LA}$ | 1.5 | 2 | 9.5 |
| $R_{SA}$ | 1.5 | 2 | 9.5 |
| $R_C$ | 1 | 1 | 5 |
| $R_{VEN}$ | 0.5 | 1 | 3.5 |
| $R_V$ | 0.5 | 0.5 | 2 |
| $C_{LA}$ | 0.1 | 0.4 | 2.1 |
| $C_{SA}$ | 1 | 1 | 4 |
| $C_C$ | 1 | 1 | 4 |
| $C_Y$ | 5 | 5 | 25 |
| $R_{CUFF-V}$ | 7 | 3 | 19 |
| X | 0 | 0.1 | 0.4 |

From these tests, we noticed many details that can be connected to physiological effects. E.g., how the presence of the plateau/dip before the maximum value in the total hemoglobin variation is strongly dependent on the cuff inflation effect on the arteries ($R_{CUFF-V}$ and X) or how the slope after the cuff is deflated is mainly related to the veins resistances and capacitances ($R_V$ and $C_V$). However, we also observed how all the variables work in tandem to obtain the final results and the ratio between them is another important factor to consider when examining the resulting shapes.

Next, we proceeded to compare each inflation/deflation period of the experimental data to the simulated curves.

To find the curves that best matched the experimental observations, we implemented an automatic fitting algorithm that evaluates point per point the mean of the absolute difference between all the simulated curves and an equivalent time interval of the experimental data. The best 100 fittings, considered as the ones with the lesser absolute mean difference, were considered. In FIG. 14 the dotted curves show example of 10 best fittings obtained with a patient.

Since for each variable only between 4 and 5 values were simulated, to increase the precision of the final estimated values the mean value for the variables in the first 10 fittings in the 100-fittings sample was used in the subsequent analysis. It is important to highlight that, if the mean values between the top 100 fittings were considered, the relative positions of the total resistances were confirmed to stay the same.

The following step consisted in finding the parameter that best represents the differences between healthy subjects and PAD patients. Therefore, is there any particular parameter or sets of parameters that can be used to classify a hemodynamic response as belonging to a PAD patient with high sensitivity and specificity Based on physiological observations, explained in the following paragraphs, we decided to focus our attention on the system's total resistance:

$$R_T = R_{LA}(t) + R_{SA} + R_C + R_{VEN} + R_V(t) \qquad (12)$$

Figure 15A:
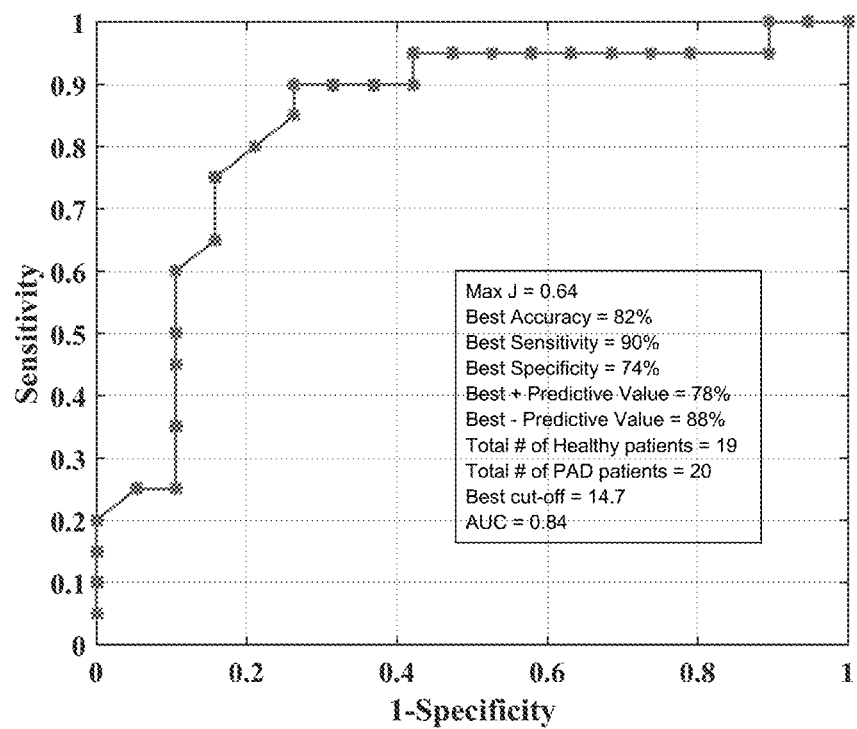
FIGS. 15A and 15B shows ROC curves obtained at rest and during a cuff inflation, respectively.
Figure 15B:
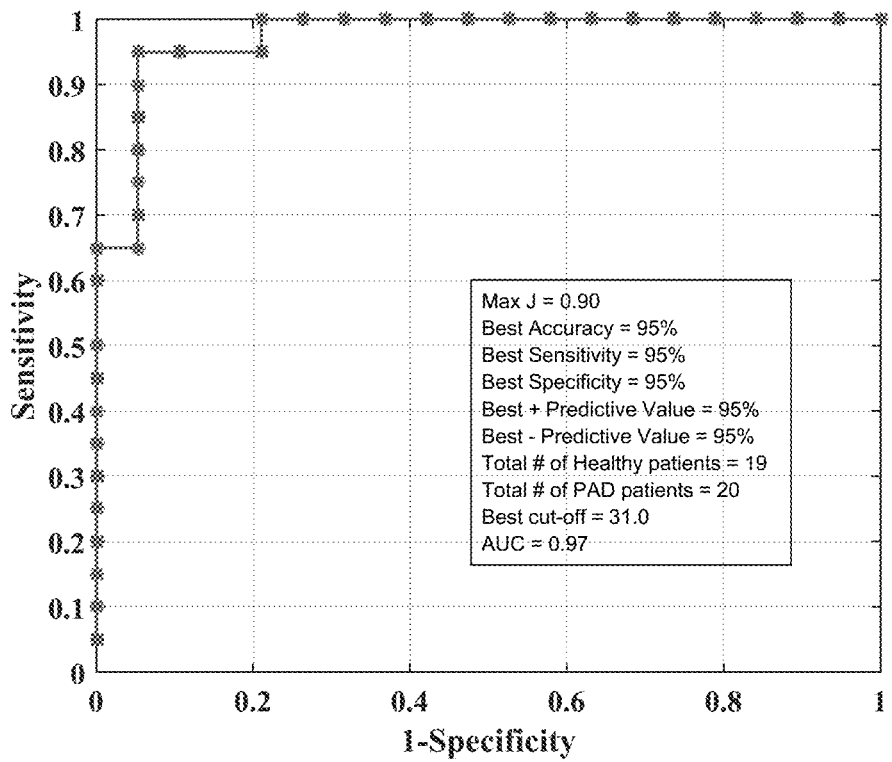

Considering the total system resistance $R_T$ as our benchmark parameter, FIGS. 15A and 15B shows the Receiving Operating Characteristic (ROC) curve plots for the data from all 39 subjects (19 healthy subjects, 10 diabetic PAD patients, and 10 non-diabetic PAD patients). More specifically, FIGS. 15A and 15B shows ROC curves obtained considering all the 34 patients. FIG. 15A considers the total system resistance at rest; FIG. 15B considers total system resistance during the cuff inflation.

Here we examined the system total resistance both at rest and during a cuff inflation and compared healthy patients to all PAD patients (non-diabetic and diabetic). In both cases, we obtained a sensitivity, specificity, and accuracy values higher than our previous study and we also observed that PAD patients react more than healthy patients to the cuff inflation, probably due to the fact that their arteries and veins internal diameters are already smaller than in healthy patients and so are completely occluded more easily and in less time. Considering the best results obtained during the cuff inflation, we found a diagnostic sensitivity, specificity, and accuracy of 95%, while the area under the curve AUC=0.97.

Figure 16:
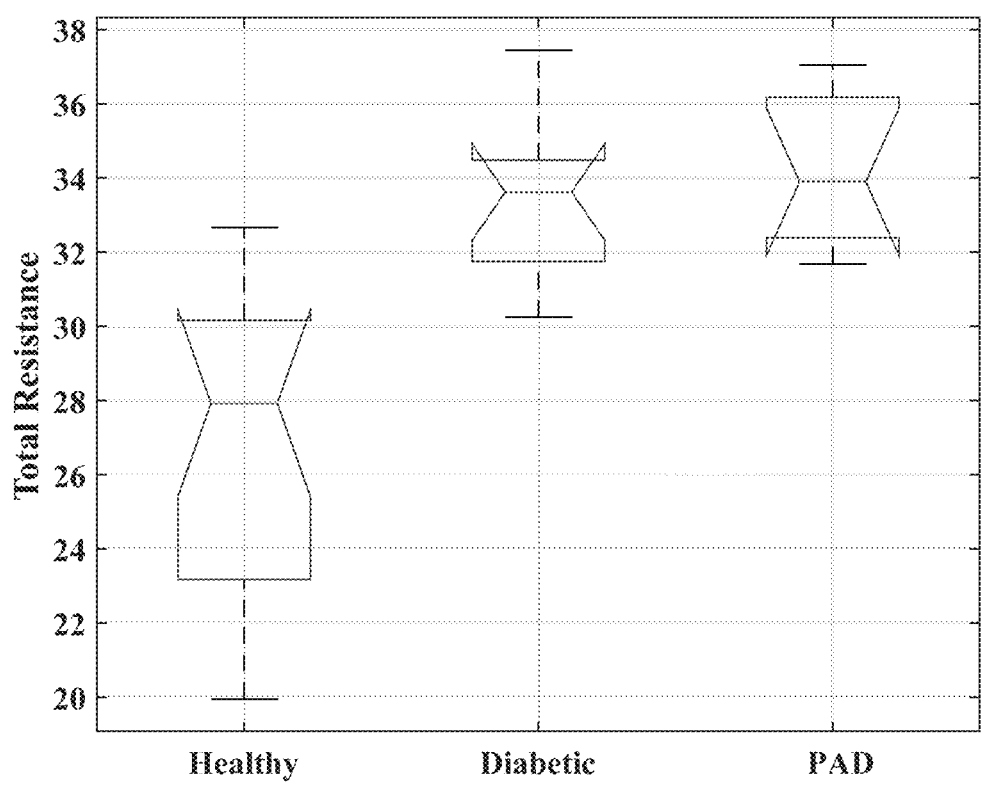
FIG. 16 is a box plot of the total system resistance during a cuff inflation estimated in healthy, diabetic PAD, and PAD patients.

Among the PAD patients, the 10 non-diabetic patients had an average ABI of 0.64±0.21 indicating moderate disease, whereas the 10 diabetic patients had an average ABI of 0.95±0.35, which would be misinterpreted as healthy vasculature. We therefore proceeded to do a statistical ANOVA analysis followed by a paired Bernoulli test using MATLAB embedded functions (anoval and multcompare) to compare between the three groups on the basis of their total resistance during cuff inflation. The results are shown in FIG. 16, which is a box plot of the total system resistance during a cuff inflation estimated in Healthy, Diabetic PAD, and PAD patients where it is possible to see a clear separation between healthy and non-diabetic PAD patients (p=0.8*10-5) and healthy and diabetic PAD patients (p=1.2*10-5). No difference however was obtained comparing diabetic and non-diabetic PAD patients (p=1).

Figure 17:
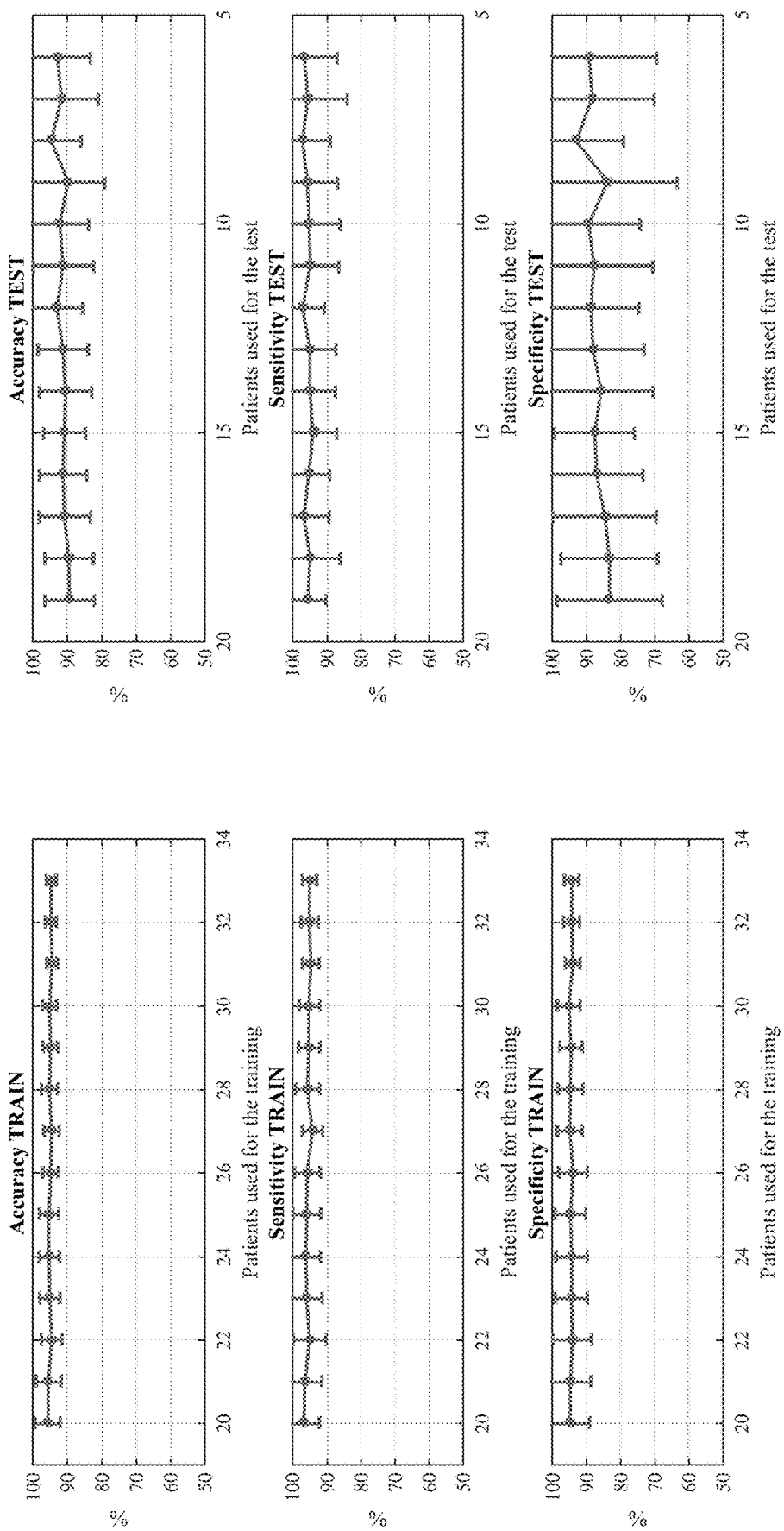
FIG. 17, depicts Train and Test results considering different combinations of patients.

A cross-validation analysis based on a statistical resampling technique used for model assessment was subsequently carried out to better validate the obtained values for accuracy, sensitivity, and specificity. To determine the optimal cut-off value for $R_T$ to differentiate between healthy and PAD patients, a training subset of patients randomly selected among all the patients was used and then the remaining patients were used as testing samples to evaluate the model's generalization. This procedure was repeated changing the size of the training subset from 20 to 34 patients, subsequently the test subset changed from 19 to 6 patients, and, in each case, 500 reshuffling of the random combinations of patients to create the train and test sets were used to increase the objectivity of the assessment, obtaining the mean and standard deviations values showed in FIG. 17, which depicts Train and Test results considering 500 different combinations of patients for each point in the graphs. A number of patients between 20 and 34 was used for the training (on the left) and the remaining patients (from 19 to 6) were used for the test.

We observed that, in the training, the mean values were always higher than 90% with standard deviations lower than 5% for all of them, whereas, in the test, accuracy and sensitivity had mean values around 90% with standard deviations lower than 10% and only the specificity had a standard deviation slightly higher (about 16%) and a mean value of about 86%.

In conclusion, examining data from 19 healthy subjects and 20 PAD patients, we found an inverse correlation between the total system resistance estimated and the healthiness of the patient—the higher the total resistance, the less healthy is the patient. This was expected from a biological point of view because if a patient is healthy, his or her arteries and veins are clean and their internal diameter is not obstructed by calcifications, like in the case of PAD patients, showing lower total system resistance to blood flow.

The mean values for sensitivity, specificity, and accuracy obtained were in all cases higher than 85%, with a total standard deviation lower than 10% for the accuracy and sensitivity and equal to 15% for the specificity. The values were obtained by selecting between 20 to 34 patients, to determine a threshold value for the total system resistance to differentiate between healthy and PAD patients, and by applying that threshold to the remaining patients subsequently.

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. An optical tomography system comprising:
   a first transducer having at least one first light source and at least one first light detector;
   a second transducer having at least one second light source and at least one second light detector; and
   a processor programmed to generate a first time-dependent indication of blood perfusion of a region corresponding to the first transducer based on an output of the at least one first light detector, and to generate a second time-dependent indication of blood perfusion of a region corresponding to the second transducer based on an output the at least one second light detector,
   wherein each of the first transducer and the second transducer is configured to releasably attach to a respective one of two separate angiosomes, and
   wherein the processor is further programmed to output, in real time during a surgical procedure, both (a) the first time-dependent indication of blood perfusion and (b) the second time-dependent indication of blood perfusion.

2. The system of claim 1, wherein the first transducer or the second transducer includes a clip configured to clip on the first toe of a human subject.

3. The system of claim 1, wherein the angiosomes are in the lower leg of a human subject.

4. The system of claim 3, wherein the first transducer or the second transducer is configured to attach to a human calf.

5. The system of claim 1, wherein the output includes graphs of hemoglobin concentration and time.

6. The system of claim 1, further comprising
   a third transducer having at least one third light source and at least one third light detector, wherein the third transducer is configured to releasably attach to an additional angiosome,
   wherein the processor is further programmed to generate a third time-dependent indication of blood perfusion of a region corresponding to the third transducer based on an output of the at least one third light detector, and
   wherein the processor is further programmed to output the third time-dependent indication of blood perfusion in real time during the surgical procedure.

7. A method of monitoring treatment of peripheral artery disease, the method comprising:
   (a) affixing a first plurality of light sources having different wavelengths and a first plurality of light detectors to a first position on a subject's limb, wherein the first position corresponds to a first angiosome of the limb;
   (b) transmitting light from the first plurality of light sources into a first portion of the subject's limb, detecting light reflected from the first portion of the subject's limb using the first plurality of light detectors, and using diffuse optical imaging to determine a level of perfusion in the first angiosome based on the detected light reflected from the first portion;
   (c) affixing a second plurality of light sources having different wavelengths and a second plurality of light detectors to a second position on a subject's limb, wherein the second position corresponds to a second angiosome of the limb; and
   (d) transmitting light from the second plurality of light sources into a second portion of the subject's limb, detecting light reflected from the second portion of the subject's limb using the second plurality of light detectors, and using diffuse optical imaging to determine a level of perfusion in the second angiosome based on the detected light reflected from the second portion,
   wherein the first plurality of light sources and the first plurality of light detectors remain affixed to the first position during steps (b) and (d), and
   wherein the second plurality of light sources and the second plurality of light detectors remain affixed to the second position during steps (b) and (d).

8. The method of claim 7, further comprising:
   (e) affixing a third plurality of light sources having different wavelengths and a third plurality of light detectors to a third position on a subject's limb, wherein the third position corresponds to a third angiosome of the limb; and
   (f) transmitting light from the third plurality of light sources into a third portion of the subject's limb, detecting light reflected from the third portion of the subject's limb using the third plurality of light detectors, and using diffuse optical imaging to determine a level of perfusion in the third angiosome based on the detected light reflected from the third portion,
   wherein the first plurality of light sources and the first plurality of light detectors remain affixed to the first position during steps (b), (d), and (f),
   wherein the second plurality of light sources and the second plurality of light detectors remain affixed to the second position during steps (b), (d), and (f), and
   wherein the third plurality of light sources and the third plurality of light detectors remain affixed to the third position during steps (b), (d), and (f).

9. The method of claim 7, wherein steps (b), (d), and (f) are each performed at a first time during which a pressure cuff is not inflated, and further comprising the step of repeating steps (b), (d), and (f) at a second time during which the pressure cuff is inflated.

10. The method of claim 7, wherein the first angiosome corresponds to a posterior tibial artery, the second angiosome corresponds to a lateral plantar artery, and the third angiosome corresponds to at least one of an anterior tibial artery and a dorsalis pedis artery.

11. The method of claim 7, further comprising
   (g) affixing a fourth plurality of light sources having different wavelengths and a fourth plurality of light detectors to a fourth position on a subject's limb, wherein the fourth position corresponds to a fourth angiosome of the limb; and
   (h) transmitting light from fourth plurality of light sources into a fourth portion of the subject's limb, detecting light reflected from the fourth portion of the subject's limb using the fourth plurality of light detectors, and using diffuse optical imaging to determine a level of perfusion in the fourth angiosome based on the detected light reflected from the fourth portion,
   wherein the first plurality of light sources and the first plurality of light detectors remain affixed to the first position during steps (b), (d), (f), and (h), wherein the second plurality of light sources and the second plurality of light detectors remain affixed to the second position during steps (b), (d), (f), and (h), wherein the third plurality of light sources and the third plurality of light detectors remain affixed to the third position during steps (b), (d), (f), and (h), and wherein the fourth plurality of light sources and the fourth plurality of light detectors remain affixed to the fourth position during steps (b), (d), (f), and (h).

12. The method of claim 11, wherein the first angiosome corresponds to a posterior tibial artery, the second angiosome corresponds to a lateral plantar artery, and the third angiosome corresponds to at least one of an anterior tibial artery and a dorsalis pedis artery.

13. The method of claim 12, wherein the fourth angiosome corresponds to a medial plantar artery.

14. The method of claim 13, wherein steps (b), (d), (f), and (h) are each performed at a first time during which a pressure cuff is not inflated, and further comprising the step of repeating steps (b), (d), (f), and (h) at a second time during which the pressure cuff is inflated.

\* \* \* \* \*